United States Patent
Lisman

(10) Patent No.: US 10,821,097 B2
(45) Date of Patent: *Nov. 3, 2020

(54) DBH INHIBITORS FOR TREATING OR PREVENTING MEMORY LOSS

(71) Applicant: Brandeis University, Waltham, MA (US)

(72) Inventor: John Lisman, Waltham, MA (US)

(73) Assignee: Brandeis University, Waltham, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/555,504

(22) Filed: Aug. 29, 2019

(65) Prior Publication Data

US 2019/0381009 A1 Dec. 19, 2019

Related U.S. Application Data

(63) Continuation of application No. 16/060,234, filed as application No. PCT/US2016/065896 on Dec. 9, 2016, now Pat. No. 10,441,573.

(60) Provisional application No. 62/265,391, filed on Dec. 9, 2015.

(51) Int. Cl.
| | |
|---|---|
| *A61K 31/417* | (2006.01) |
| *A61K 31/145* | (2006.01) |
| *A61K 31/198* | (2006.01) |
| *A61K 31/4458* | (2006.01) |
| *A61K 45/06* | (2006.01) |
| *A61P 25/28* | (2006.01) |

(52) U.S. Cl.
CPC .......... *A61K 31/417* (2013.01); *A61K 31/145* (2013.01); *A61K 31/198* (2013.01); *A61K 31/4458* (2013.01); *A61K 45/06* (2013.01); *A61P 25/28* (2018.01); *A61K 2300/00* (2013.01)

(58) Field of Classification Search
CPC .. A61K 31/417; A61K 31/145; A61K 31/198; A61P 25/28
USPC ........................................ 514/392, 317, 567
See application file for complete search history.

(56) References Cited

U.S. PATENT DOCUMENTS

| | | | |
|---|---|---|---|
| 3,657,250 A | 4/1972 | Bruderlein et al. | |
| 4,933,324 A | 6/1990 | Shashoua | |
| 4,939,174 A | 7/1990 | Shashoua | |
| 5,112,596 A | 5/1992 | Malfroy-Camine | |
| 5,206,264 A | 4/1993 | Marangos | |
| 5,268,164 A | 12/1993 | Kozarich et al. | |
| 5,373,021 A | 12/1994 | Marangos | |
| 5,994,932 A | 11/1999 | Ando | |
| 6,107,499 A | 8/2000 | Shashoua | |
| 6,258,836 B1 | 7/2001 | Shashoua | |
| 6,407,137 B2 | 6/2002 | Shashoua | |
| 10,441,573 B2 * | 10/2019 | Lisman | A61K 31/198 |
| 2002/0103162 A1 | 8/2002 | Epstein et al. | |
| 2002/0111384 A1 | 8/2002 | Boudrie et al. | |
| 2002/0128319 A1 | 9/2002 | Koo et al. | |
| 2005/0112543 A1 | 5/2005 | Bush et al. | |
| 2011/0086845 A1 | 4/2011 | Feinstein et al. | |
| 2014/0080800 A1 | 3/2014 | Holson et al. | |
| 2018/0369201 A1 | 12/2018 | Lisman | |

FOREIGN PATENT DOCUMENTS

| | | |
|---|---|---|
| WO | WO-2001/078721 A1 | 10/2001 |
| WO | WO-02/17919 A2 | 3/2002 |
| WO | WO-2010/132128 A1 | 11/2010 |
| WO | WO-2012/024616 A1 | 2/2012 |
| WO | WO-2013/123426 A1 | 8/2013 |
| WO | WO-2017/100623 A1 | 6/2017 |

OTHER PUBLICATIONS

Access FDA, Northera (droxidopa) Drug Information, Reference ID: 3544888, 10 pages (last revised Feb. 2014), <http://www.accessdata.fda.gov/drugsatfda_docs/label/2014/203202lbl.pdf>. Retrieved Nov. 15, 2018.

Bethus, I. et al., Dopamine and memory: modulation of the persistence of memory for novel hippocampal NMDA receptor-dependent paired associates, The Journal of Neurosciences: The Official Journal of the Society of Neuroscience, 30(5):1610-1618 (2010).

Bondareff, W. et al., Loss of neurons of origin of the adrenergic projection to cerebral cortex (nucleus locus ceruleus) in senile dementia, Neurology, 32(2):164-168 (1982).

Bosch, M. et al., Structural and molecular remodeling of dendritic spine substructures during long-term potentiation, Neuron, 82(2):444-459 (2014).

Braak, H. and Del Tredici, K., Where, when, and in what form does sporadic Alzheimer's disease begin?, Curr. Opin. Neurol., 25(6):708-714 (2012).

Bruchas, M.R. and Chavkin, C., Kinase cascades and ligand-directed signaling at the kappa opioid receptor, Psychopharmacology (Berl), 210(2):137-147 (2010).

ClinicalTrials.gov, Study of Safety and Potential Efficacy of SYN117 in Cocaine Dependent Volunteers, NCT00656357, Biotie Therapies Inc., 7 pages (last updated Aug. 17, 2018), <https://www.clinicaltrials.gov/ct2/show/study/NCT00656357>. Retrieved Nov. 15, 2018.

Comery, T. A. et al, Acute gamma-secretase inhibition improves contextual fear conditioning in the Tg2576 mouse model of Alzheimer's disease, J. Neurosci., 25(39): 8898-902 (2005).

Cubells et al., Human Genetics of Plasma DBH Activity in Cocaine Dependence, ACNP 2005 Annual Meeting, Panel Session, p. S1 (Dec. 12, 2005).

(Continued)

*Primary Examiner* — Kevin E Weddington
(74) *Attorney, Agent, or Firm* — Choate, Hall & Stewart LLP; John P. Rearick; Nicholas J. Pace

(57) ABSTRACT

The present invention relates to the use of DBH inhibitors (e.g., disulfiram and Nepicastat), and pharmaceutical compositions thereof, for treating subjects with certain types of memory loss, for instance memory loss associated with a neurodegenerative disease, disorder, or condition, such as Alzheimer's Disease.

20 Claims, 1 Drawing Sheet

(56) References Cited

OTHER PUBLICATIONS

Devoto, P. et al., The dopamine beta-hydroxylase inhibitor nepicastat increases dopamine release and potentiates psychostimulant? induced dopamine release in the prefrontal cortex, Addition Biology, 19(4):612-622 (2014).

Drugs.com, Atomoxetine Dosage Guide with Precautions, 3 pages (medically reviewed Sep. 1, 2017), <http://www.drugs.com/dosage/atomoxetine.html>. Retrieved Nov. 15, 2018.

Drugs.com, Disulfiram Dosage Guide with Precautions, 3 pages (medically reviewed Mar. 13, 2018),<http://www.drugs.com/dosage/disulfiram.html#Usual_adult_Dose_for_alcohol_dependence>. Retrieved Nov. 15, 2018.

Frey, U. et al., Dopaminergic antagonists prevent long-term maintenance of posttetanic LTP in the CA1 region of rat hippocampal slices, Brain Research, 522(1):69-75 (1990).

Gannon, M. et al., Noradrenergic dysfunction in Alzheimer's disease, Frontiers in Neuroscience, 9:200 (2015).

Gaval-Cruz, M. et al., Chronic Inhibition of Dopamine Beta-Hydroxylase Facilitates Behavioral Responses to Cocaine in Mice, PLoS ONE, 7(11):1-9 (2012).

Giese, K.P. et al., Autophosphorylation at Thr286 of the a Calcium-Calmodulin Kinase II in LTP and Learning, Science, 279(5352):870-873 (1998).

Goldstein, M. and Nakajima, K., The effect of disulfiram on catecholamine levels in the brain, Journal of Pharmacology and Experimental Therapeutics, 157(1):96-102 (1967).

Hammerschmidt, T. et al., Selective loss of noradrenaline exacerbates early cognitive dysfunction and synaptic deficits in APP/PS1 mice, Biol. Psychiatry, 73(5):454-463 (2013).

Hopkins, W.F. and Johnston, D., Noradrenergic enhancement of long-term potentiation at mossy fiber synapses in the hippocampus, Journal of Neurophysiology, 59(2):667-687 (1988).

Hsiao, K. et al, Correlative memory deficits, Abeta elevation, and amyloid plaques in transgenic mice, Science, 274(5284): 99-102 (1996).

Huang, Y.Y. and Kandel, E.R., D1/D5 receptor agonists induce a protein synthesis-dependent late potentiation in the CA1 region of the hippocampus, PNAS USA, 92(7):2446-2450 (1995).

International Search Report for PCT/US2016/065896, 3 pages (dated Feb. 17, 2017).

Kalinin, S. et al., Noradrenaline deficiency in brain increases beta-amyloid plaque burden in an animal model of Alzheimer's disease, Neurobiol. Aging, 28(8):1206-1214 (2007).

Kalinin, S. et al., The noradrenaline precursor L-DOPS reduces pathology in a mouse model of Alzheimer's disease, Neurobiol. Aging, 33(8):1651-1663 (2012).

Li, S. et al., Dopamine-dependent facilitation of LTP induction in hippocampal CA1 by exposure to spatial novelty, Nature Neuroscience, 6:526-531 (2003).

Li, S. et al., Environmental Novelty Activates β2-Adrenergic Signaling to Prevent the Impairment of Hippocampal LTP by Aβ Oligomers, Neuron, 77(5):929-941 (2013).

Lisman, J. et al., A neoHebbian framework for episodic memory; role of dopamine-dependent late LTP, Trends Neurosci., 34(1):536-547 (2011).

Lockrow, J.P. et al., Age-Related Neurodegeneration and Memory Loss in Down Syndrome, Current Gerontology and Geriatrics Research, 463909, 13 pages (2012).

Marien, M.R. et al., Noradrenergic mechanisms in neurodegenerative diseases: a theory, Brain Research Reviews, 45(1):38-78 (2004).

Morihara, T. et al., Selective inhibition of Alpha beta production by NSAID R-enantiomers, J. Neurochem, 83(4):1009-1012 (2002).

Moudy, A.M. et al., Development of dopamine-beta-hydroxylase-positive fiber innervation of the rat hippocampus, Synapse, 15(4):307-318 (1993).

Mucke, L. et al., High-Level Neuronal Expression of A?1-42 in Wild-Type Human Amyloid Protein Precursor Transgenic Mice: Synaptotoxicity without Plaque Formation, The Journal of Neuroscience, 20(11):4050-4058 (2000).

Nicoll, R.A., Expression mechanisms underlying long-term potentiation: a postsynaptic view, Philosophical Transactions of the Royal Society of London, Series B, Biological Sciences, 358(1432):721-726 (2003).

Nobili, A. et al, Dopamine neuronal loss contributes to memory and reward dysfunction in a model of Alzheimer's disease, Nat. Commun., 8: 14727 (2017).

Ortiz, O. et al., Associative Learning and CA3-CA1 Synaptic Plasticity Are Impaired in D1R Null, Drd1a-/- Mice and in Hippocampal siRNA Silenced Drd1a Mice, The Journal of Neuroscience, 30(37):12288-12300 (2010).

Otmakhova, N.A. and Lisman, J.E., D1/D5 Dopamine Receptors Inhibit Depotentiation at CA1 Synapses via cAMP-Dependent Mechanism, The Journal of Neuroscience, 18(4):1270-1279 (1998).

Robertson, S.D. et al., Developmental origins of central norepinephrine neuron diversity, Nat. Neurosci., 16(8):1016-1023 (2013).

Roche Products (New Zealand) Limited, MADOPAR Data Sheet, 12 pages (2016), <http://www.medsafe.govt.nz/profs/datasheet/m/Madoparcapdisptab.pdf>. Retrieved Nov. 15, 2018.

Ross, S.B. and Stenfors, C., DSP4, a selective neurotoxin for the locus coeruleus noradrenergic system. A review of its mode of action, Neurotox. Res., 27(1):15-30 (2015).

Rossato, J.I. et al., Dopamine Controls Persistence of Long-Term Memory Storange, Science, 325:1017-1020 (2009).

Rozeske, R. R. et al, Prefrontal neuronal circuits of contextual fear conditioning, Genes Brain Behav., 14(1): 22-36 (2015).

Schroeder, J.P. et al., Disulfiram Attenuates Drug-Primed Reinstatement of Cocaine Seeking via Inhibition of Dopamine β-Hydroxylase Neuropsychopharmacology, 35:2440-2449 (2010).

Shen, H. et al, Effects of benserazide on L-DOPA-derived extracellular dopamine levels and aromatic L-amino acid decarboxylase activity in the striatum of 6-hydroxydopamine-lesioned rats, Tohuku J. Exp. Med., 199(3): 149-59 (2003).

Smith, C.C. and Greene, R.W., CNS Dopamine Transmission Mediated by Noradrenergic Innervation, The Journal of Neuroscience, 32(18):6072-6080 (2012).

Sonneborn, A. et al., A physiological role for locus coeruleus dopamine, Society for Neuroscience, Program 253.30, Poster V48, Presented Oct. 18, 2015. <http://www.abstractonline.com/Plan/AbstractPrintView.aspx?mID=374 . . . >. Retrieved Nov. 29, 2018.

Stanley, W.C., Catecholamine modulatory effects of nepicastat (RS-25560-197), a novel, potent and selective inhibitor of dopamine-beta-hydroxylase, British Journal of Pharmacology, 121(8):1803-1809 (1997).

Szot, P. et al., Compensatory Changes in the Noradrenergic Nervous System in the Locus Ceruleus and Hippocampus of Postmortem Subjects with Alzheimer's Disease and Dementia with Lewy Bodies, The Journal of Neuroscience, 26(2):467-478 (2006).

Takahashi, Y. et al., Sulindac sulfide is a noncompetitive gamma-secretase inhibitor that preferentially reduces Abeta 42 generation, J. Biol. Chem., 278(20):18644-18670 (2003).

Takeuchi, T. et al., Catecholaminergic enhancement of initial memory consolidation in mice, Society for Neuroscience, Program 535.09, Poster BB14, Presented Oct. 20, 2015. <http://www.:abstractonline.com/Plan/AbstractPrintView.aspx?mID=374 . . . >. Retrieved Nov. 29, 2108.

Thomas, S.A. and Palmiter, R.D., Disruption of the dopamine ß-hydroxylase gene in mice suggests roles for norepinephrine in motor function, learning, and memory, Behavioral Neuroscience, 111(3):579-589 (1997).

Vardy, E. et al., A New DREADD Facilitates the Multiplexed Chemogenetic Interrogation of Behavior, Neuron, 86(4):936-946 (2015).

Wang, S.H. et al., Relevance of synaptic tagging and capture to the persistence of long-term potentiation and everyday spatial memory, PNAS, 107(45):19537-19542 (2010).

Weggen, S. et al., A subset of NSAIDs lower amyloidogenic Aß42 independently of cyclooxygenase activity, Nature, 414(6860):212-216 (2001).

Written Opinion for PCT/US2016/065896, 7 pages (dated Feb. 17, 2017).

(56) References Cited

OTHER PUBLICATIONS

Zarow, C. et al., Neuronal Loss Is Greater in the Locus Coeruleus Than Nucleus Basalis and Substantia Nigra in Alzheimer and Parkinson Diseases, Arch Neurol., 60(3):337-341 (2003).

* cited by examiner

DBH INHIBITORS FOR TREATING OR PREVENTING MEMORY LOSS

CROSS-REFERENCE TO RELATED APPLICATIONS

This application is a continuation of U.S. patent application Ser. No. 16/060,234, filed Jun. 7, 2018 (now U.S. Pat. No. 10,441,573), which is a national phase application under 35 U.S.C. § 371 of PCT international application number PCT/US2016/065896, filed Dec. 9, 2016, which claims priority to U.S. provisional application Ser. No. 62/265,391, filed Dec. 9, 2015, the entirety of each of which is hereby incorporated herein by reference.

BACKGROUND

Much has been learned about how episodic memory is encoded in the hippocampus (reviewed in (Hell & Ehlers, 2008). In this structure, the strength of synapses can be changed by experience through a process called long-term potentiation (LTP). It has been shown that mutations that interfere with LTP produce profound deficits in memory (Giese, Fedorov, Filipkowski, & Silva, 1998). There has therefore been a great deal of effort to understand the cellular and molecular mechanisms of this process. The LTP in the stratum radiatum of the CA1 hippocampal region has served as the model system for the field. An important insight is that LTP has both early and late phases, and that these two phases have very different properties. Early LTP (~1 hr) depends on modifications of the existing synaptic structure (e.g., phosphorylation of GluR1 and stargazin (Nicoll, 2003)), whereas late LTP depends on protein synthesis and trans-synaptic enlargement of the synapse (Bosch et al., 2014).

The neuromodulator dopamine has been shown to have a necessary role in late LTP and late memory. It has been shown that late LTP (but not early LTP) is strongly inhibited by dopamine (D1) antagonists (Frey, Schroeder, & Matthies, 1990; Gao et al., 2009; Huang & Kandel, 1995; Li, Cullen, Anwyl, & Rowan, 2003; Otmakhova & Lisman, 1998)). This dopamine requirement has been further verified by knockout of dopamine receptors, by dopamine depletion experiments (reviewed by (Lisman et al., 2011)) and by reducing D1 receptors using siRNA (Ortiz et al., 2010). The present disclosure relates to technologies that can increase dopamine levels and/or can otherwise improve memory or treat one or more diseases, disorders or conditions including, for example, Alzheimer's disease.

SUMMARY

The present invention encompasses the finding that agents that inhibit the enzyme dopamine beta-hydroxylase (i.e., DBH inhibitors) can be effective in treating or preventing certain types of memory loss, for instance memory loss associated with a neurodegenerative disease, disorder, or condition such as Alzheimer's disease. Without wishing to be bound by any particular theory, the present disclosure proposes that failure of memory in Alzheimer's disease occurs at least in part because dopamine is not adequately provided as a result of the reduced number of LC axons in patients with Alzheimer's disease. According to the present disclosure, in light of this insight, methods for enhancing dopamine release from remaining LC axons may be therapeutic. As described above and herein, one target for treatment is dopamine-beta-hydroxylase (DBH), the enzyme that converts dopamine to noradrenaline.

In some embodiments, the invention provides methods of treating a subject suffering from or susceptible to certain types of memory loss, for instance memory loss associated with a neurodegenerative disease, disorder, or condition such as Alzheimer's disease, with a DBH inhibitor (e.g., disulfiram or Nepicastat). In certain embodiments, the subject is an adult human. In some such embodiments, the neurodegenerative disease, disorder, or condition is Alzheimer's disease. In some such embodiments, Alzheimer's disease is early stage Alzheimer's disease.

In some embodiments, the invention provides methods of treating a subject suffering from or susceptible to a neurodegenerative disease, disorder, or condition such as Alzheimer's disease, with a DBH inhibitor (e.g., disulfiram or Nepicastat). In certain embodiments, the subject is an adult human. In some such embodiments, the neurodegenerative disease, disorder, or condition is Alzheimer's disease. In some such embodiments, the Alzheimer's disease is early stage Alzheimer's Disease.

In some embodiments, the present invention provides methods of enhancing long term memory in a subject using a DBH inhibitor (e.g., disulfiram or Nepicastat). In certain embodiments, the subject is a mammal. In some such embodiments, the subject is a rat or mouse. In some such embodiments, the subject is an adult human.

In some embodiments, the present invention provides methods of inhibiting dopamine conversion using a DBH inhibitor (e.g., disulfiram or Nepicastat). Inhibiting dopamine conversion may occur in vivo (e.g., in a subject as described herein) or in vitro (e.g., in a cell or assay). In some such embodiments, inhibition of dopamine conversion occurs in vivo in a subject as described herein. In some such embodiments, the subject is a mammal. In some such embodiments, the subject is a rat or mouse. In some such embodiments, the subject is an adult human.

In some embodiments, the invention provides methods of treating a subject suffering from or susceptible to memory loss associated with degeneration of the LC with a DBH inhibitor (e.g., disulfiram or Nepicastat). In some such embodiments, the subject is a mammal. In some such embodiments, the subject is a rat or mouse. In some such embodiments, the subject is an adult human.

In some embodiments, the present invention provides methods of increasing levels of dopamine in the LC of a subject using a DBH inhibitor (e.g., disulfiram or Nepicastat). In some such embodiments, the subject is a mammal. In some such embodiments, the subject is a rat or mouse. In some such embodiments, the subject is an adult human.

In some embodiments, the present invention provides methods of preventing or reducing amyloid beta plaque formation in the brain of a subject using a DBH inhibitor (e.g., disulfiram or Nepicastat). In some such embodiments, the subject is a mammal. In some such embodiments, the subject is a rat or mouse. In some such embodiments, the subject is an adult human. In some such embodiments, the subject is an adult human suffering from or susceptible to Alzheimer's disease.

In some embodiments, the present invention provides methods for assessing and/or characterizing one or more DBH inhibitors for enhancement of dopamine release from LC axons. In some embodiments, the present invention provides methods of assessing and/or characterizing memory enhancement using DBH inhibitors.

In some embodiments, the present invention contemplates use of a DBH inhibitor (e.g., disulfiram or Nepicastat) in accordance with any of the above-described methods, in combination with one or more agents that ameliorate noradrenaline reduction associated with use of a DBH inhibitor (e.g., L-DOPS, also known as droxidopa). In some embodiments, the present invention contemplates use of a DBH inhibitor (e.g., disulfiram or Nepicastat) in accordance with any of the above-described methods, in combination with one or more agents and/or therapies known to increase levels of dopamine in a subject and/or to inhibit reuptake of dopamine in a subject. In some embodiments, the present invention contemplates use of a DBH inhibitor (e.g., disulfiram or Nepicastat) in accordance with any of the above-described methods, in combination with one or more agents that ameliorate noradrenaline reduction associated with use of a DBH inhibitor (e.g., L-DOPS), and further in combination with one or more agents and/or therapies known to increase levels of dopamine in a subject and/or to inhibit reuptake of dopamine in a subject. In some embodiments, the subject is undergoing treatment for Alzheimer's Disease. Exemplary such treatments are known in the medical arts and contemplated herein for use in combination with methods of the present invention.

All publications and patent documents cited in this application are incorporated herein by reference in their entirety.

Definitions

About: The term "about" or "approximately", when used herein in reference to a value, refers to a value that is similar, in context to the referenced value. In general, those skilled in the art, familiar with the context, will appreciate the relevant degree of variance encompassed by "about" in that context. For example, in some embodiments, the term "about" may encompass a range of values that within 25%, 20%, 19%, 18%, 17%, 16%, 15%, 14%, 13%, 12%, 11%, 10%, 9%, 8%, 7%, 6%, 5%, 4%, 3%, 2%, 1%, or less of the referred value.

Administration: As used herein, the term "administration" typically refers to the administration of a composition to a subject or system to achieve delivery of an agent that is, or is included in, the composition. Those of ordinary skill in the art will be aware of a variety of routes that may, in appropriate circumstances, be utilized for administration to a subject, for example a human. For example, in some embodiments, administration may be ocular, oral, parenteral, topical, etc. In some particular embodiments, administration may be bronchial (e.g., by bronchial instillation), buccal, dermal (which may be or comprise, for example, one or more of topical to the dermis, intradermal, interdermal, transdermal, etc), enteral, intra-arterial, intradermal, intragastric, intramedullary, intramuscular, intranasal, intraperitoneal, intrathecal, intravenous, intraventricular, within a specific organ (e.g. intrahepatic), mucosal, nasal, oral, rectal, subcutaneous, sublingual, topical, tracheal (e.g., by intratracheal instillation), vaginal, vitreal, etc. In some embodiments, administration may involve only a single dose. In some embodiments, administration may involve application of a fixed number of doses. In some embodiments, administration may involve dosing that is intermittent (e.g., a plurality of doses separated in time) and/or periodic (e.g., individual doses separated by a common period of time) dosing. In some embodiments, administration may involve continuous dosing (e.g., perfusion) for at least a selected period of time.

Agent: In general, the term "agent", as used herein, may be used to refer to a compound or entity of any chemical class including, for example, a polypeptide, nucleic acid, saccharide, lipid, small molecule, metal, or combination or complex thereof. In appropriate circumstances, as will be clear from context to those skilled in the art, the term may be utilized to refer to an entity that is or comprises a cell or organism, or a fraction, extract, or component thereof. Alternatively or additionally, as context will make clear, the term may be used to refer to a natural product in that it is found in and/or is obtained from nature. In some instances, again as will be clear from context, the term may be used to refer to one or more entities that is man-made in that it is designed, engineered, and/or produced through action of the hand of man and/or is not found in nature. In some embodiments, an agent may be utilized in isolated or pure form; in some embodiments, an agent may be utilized in crude form. In some embodiments, potential agents may be provided as collections or libraries, for example that may be screened to identify or characterize active agents within them. In some cases, the term "agent" may refer to a compound or entity that is or comprises a polymer; in some cases, the term may refer to a compound or entity that comprises one or more polymeric moieties. In some embodiments, the term "agent" may refer to a compound or entity that is not a polymer and/or is substantially free of any polymer and/or of one or more particular polymeric moieties. In some embodiments, the term may refer to a compound or entity that lacks or is substantially free of any polymeric moiety.

Animal: As used herein, the term "animal" refers to any member of the animal kingdom. In some embodiments, "animal" refers to humans, at any stage of development. In some embodiments, "animal" refers to non-human animals, at any stage of development. In certain embodiments, the non-human animal is a mammal (e.g., a rodent, a mouse, a rat, a rabbit, a monkey, a dog, a cat, a sheep, cattle, a primate, and/or a pig). In some embodiments, animals include, but are not limited to, mammals, birds, reptiles, amphibians, fish, and/or worms. In some embodiments, an animal may be a transgenic animal, a genetically-engineered animal, and/or a clone.

Associated with: Two events or entities are "associated" with one another, as that term is used herein, if the presence, level and/or form of one is correlated with that of the other. For example, a particular entity (e.g., polypeptide, genetic signature, metabolite, microbe, etc) is considered to be associated with a particular disease, disorder, or condition, if its presence, level and/or form correlates with incidence of and/or susceptibility to the disease, disorder, or condition (e.g., across a relevant population).

Combination therapy: The phrase "combination therapy," as used herein, refers to those situations in which two or more different pharmaceutical agents are administered in overlapping regimens so that the subject is simultaneously exposed to both agents. As used herein, the term "combination" or "combined," as used in the context of combination therapies, refer to the simultaneous or sequential administration of therapeutic agents in accordance with this invention such that the subject is simultaneously exposed to both agents. In some embodiments, the two or more therapeutic regimens are administered in overlapping dosing regimens. In some embodiments, administration of combination therapy may involve administration of one or more therapeutic agents or modalities to a subject receiving the other agent(s) or modality. In some embodiments, combination therapy does not necessarily require that individual agents be administered together in a single composition (or even necessarily at the same time). In some embodiments, two or more therapeutic agents or modalities of a combination therapy are administered to a subject separately, e.g., in separate compositions, via separate administration routes (e.g., one agent orally and another agent intravenously), and/or at different time points. In some embodiments, two or more therapeutic agents may be administered together in a combination composition, or even in a combination compound (e.g., as part of a single chemical complex or covalent entity), via the same administration route, and/or at the same time.

DBH inhibitor: The phrase "DBH inhibitor" refers to a class of compounds characterized as having an ability to inhibit the enzyme dopamine beta-hydroxylase, which enzyme converts dopamine to noradrenaline (also known as norepinephrine (NE)) in noradrenergic cells. DBH inhibitors are known in the art and include, but are not limited to, disulfiram and Nepicastat. In some embodiments, a DBH inhibitor is a selective inhibitor (e.g., Nepicastat). In some embodiments, a DBH inhibitor is not a selective inhibitor (e.g., disulfiram).

Dosing regimen: A "dosing regimen" (or "therapeutic regimen"), as that term is used herein, is a set of unit doses (typically more than one) that are administered individually to a subject, typically separated by periods of time. In some embodiments, a given therapeutic agent has a recommended dosing regimen, which may involve one or more doses. In some embodiments, a dosing regimen is an FDA approved regimen for a particular agent for a particular indication, or is otherwise known in the medical arts for treating a particular indication. In some embodiments, a dosing regimen comprises a plurality of doses each of which are separated from one another by a time period of the same length; in some embodiments, a dosing regime comprises a plurality of doses and at least two different time periods separating individual doses.

Intraperitoneal: The phrases "intraperitoneal administration" and "administered intraperitonealy" as used herein have their art-understood meaning referring to administration of a compound or composition into the peritoneum of a subject.

In vitro: As used herein, the term "in vitro" refers to events that occur in an artificial environment, e.g., in a test tube or reaction vessel, in cell culture, etc., rather than within an organism (e.g., animal, plant, and/or microbe).

In vivo: As used herein, the term "in vivo" refers to events that occur within an organism (e.g., animal, plant, and/or microbe).

Oral: The phrases "oral administration" and "administered orally" as used herein have their art-understood meaning referring to administration by mouth of a compound or composition.

Parenteral: The phrases "parenteral administration" and "administered parenterally" as used herein have their art-understood meaning referring to modes of administration other than enteral and topical administration, usually by injection, and include, without limitation, intravenous, intramuscular, intraarterial, intrathecal, intracapsular, intraorbital, intracardiac, intradermal, intraperitoneal, transtracheal, subcutaneous, subcuticular, intraarticulare, subcapsular, subarachnoid, intraspinal, and intrastemal injection and infusion.

Patient: As used herein, the term "patient", "subject", or "test subject" refers to any organism to which a DBH inhibitor (e.g., disulfiram or Nepicastat) is administered in accordance with the present invention e.g., for experimental, diagnostic, prophylactic, and/or therapeutic purposes. Typical subjects include animals (e.g., mammals such as mice, rats, rabbits, non-human primates, and humans; insects; worms; etc.). In some embodiments, a subject may be suffering from, and/or susceptible to a disease, disorder, and/or condition (e.g., a neurodegenerative disease, a disease, disorder or condition associated with memory loss, AD, etc.).

Pharmaceutically acceptable: The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

Prevention: The term "prevention", as used herein, refers to a delay of onset, and/or reduction in frequency and/or severity of one or more symptoms of a particular disease, disorder or condition. In some embodiments, prevention is assessed on a population basis such that an agent is considered to "prevent" a particular disease, disorder or condition if a statistically significant decrease in the development, frequency, and/or intensity of one or more symptoms of the disease, disorder or condition is observed in a population susceptible to the disease, disorder, or condition. Prevention may be considered complete when onset of a disease, disorder or condition has been delayed for a predefined period of time.

Prodrug: A general, a "prodrug", as that term is used herein and as is understood in the art, is an entity that, when administered to an organism, is metabolized in the body to deliver a therapeutic agent of interest. Various forms of "prodrugs" are known in the art. For examples of such prodrug derivatives, see:

a) *Design of Prodrugs*, edited by H. Bundgaard, (Elsevier, 1985) *and Methods in Enzymology,* 42:309-396, edited by K. Widder, et al. (Academic Press, 1985);
    b) A Textbook of Drug Design and Development, edited by Krogsgaard-Larsen;
    c) Bundgaard, Chapter 5 "Design and Application of Prodrugs", by H. Bundgaard, p. 113-191 (1991);
    d) Bundgaard, *Advanced Drug Delivery Reviews*, 8:1-38 (1992);
    e) Bundgaard, et al., *Journal of Pharmaceutical Sciences,* 77:285 (1988); and
    f) Kakeya, et al., *Chem. Pharm. Bull.,* 32:692 (1984).

The methods and structures described herein relating to a DBH inhibitor (e.g., disulfiram or Nepicastat) also apply to pharmaceutically acceptable salts thereof.

Substantially: As used herein, the term "substantially" refers to the qualitative condition of exhibiting total or near-total extent or degree of a characteristic or property of interest. One of ordinary skill in the biological arts will understand that biological and chemical phenomena rarely, if ever, go to completion and/or proceed to completeness or achieve or avoid an absolute result. The term "substantially" is therefore used herein to capture the potential lack of completeness inherent in many biological and/or chemical phenomena.

Suffering from: An individual who is "suffering from" a disease, disorder, and/or condition has been diagnosed with and/or displays one or more symptoms of a disease, disorder, and/or condition.

Susceptible to: An individual who is "susceptible to" a disease, disorder, and/or condition is one who has a higher risk of developing the disease, disorder, and/or condition than does a member of the general public. In some embodiments, an individual who is susceptible to a disease, disorder and/or condition may not have been diagnosed with the disease, disorder, and/or condition. In some embodiments, an individual who is susceptible to a disease, disorder, and/or condition may exhibit symptoms of the disease, disorder, and/or condition. In some embodiments, an individual who is susceptible to a disease, disorder, and/or condition may not exhibit symptoms of the disease, disorder, and/or condition. In some embodiments, an individual who is susceptible to a disease, disorder, and/or condition will develop the disease, disorder, and/or condition. In some embodiments, an individual who is susceptible to a disease, disorder, and/or condition will not develop the disease, disorder, and/or condition.

Therapeutic agent: As used herein, the phrase "therapeutic agent" refers to any agent that, when administered to a subject, has a therapeutic effect and/or elicits a desired biological and/or pharmacological effect. In some embodiments, a therapeutic agent is any substance that can be used to alleviate, ameliorate, relieve, inhibit, prevent, delay onset of, reduce severity of, and/or reduce incidence of one or more symptoms or features of a disease, disorder, and/or condition.

Therapeutically effective amount: As used herein, the term "therapeutically effective amount" means an amount of a substance (e.g., a therapeutic agent, composition, and/or formulation) that elicits a desired biological response when administered as part of a therapeutic regimen. In some embodiments, a therapeutically effective amount of a substance is an amount that is sufficient, when administered to a subject suffering from or susceptible to a disease, disorder, and/or condition, to treat, diagnose, prevent, and/or delay the onset of the disease, disorder, and/or condition. As will be appreciated by those of ordinary skill in this art, the effective amount of a substance may vary depending on such factors as the desired biological endpoint, the substance to be delivered, the target cell or tissue, etc. For example, the effective amount of compound in a formulation to treat a disease, disorder, and/or condition is the amount that alleviates, ameliorates, relieves, inhibits, prevents, delays onset of, reduces severity of and/or reduces incidence of one or more symptoms or features of the disease, disorder, and/or condition. In some embodiments, a therapeutically effective amount is administered in a single dose; in some embodiments, multiple unit doses are required to deliver a therapeutically effective amount.

Treat: As used herein, the term "treat," "treatment," or "treating" refers to any method used to partially or completely alleviate, ameliorate, relieve, inhibit, prevent, delay onset of, reduce severity of, and/or reduce incidence of one or more symptoms or features of a disease, disorder, and/or condition. Treatment may be administered to a subject who does not exhibit signs of a disease, disorder, and/or condition. In some embodiments, treatment may be administered to a subject who exhibits only early signs of the disease, disorder, and/or condition, for example for the purpose of decreasing the risk of developing pathology associated with the disease, disorder, and/or condition.

Systemic: The phrases "systemic administration," "administered systemically," "peripheral administration," and "administered peripherally" as used herein have their art-understood meaning referring to administration of a compound or composition such that it enters the recipient's system.

Unit dose: The expression "unit dose" as used herein refers to a physically discrete unit of a pharmaceutical composition, formulated for administration to a subject. In many embodiments, a unit dose contains a predetermined quantity of an active agent. In some embodiments, a unit dose contains an entire single dose of the agent. In some embodiments, more than one unit dose is administered to achieve a total single dose. In some embodiments, administration of multiple doses is required, or expected to be required, in order to achieve an intended effect. The unit dose may be, for example, a volume of liquid (e.g., an acceptable carrier) containing a predetermined quantity of one or more therapeutic agents, a predetermined amount of one or more therapeutic agents in solid form, a sustained release formulation or drug delivery device containing a predetermined amount of one or more therapeutic agents, etc. It will be appreciated that a unit dose may contain a variety of components in addition to the therapeutic agent(s). For example, acceptable carriers (e.g., pharmaceutically acceptable carriers), diluents, stabilizers, buffers, preservatives, etc., may be included as described infra. It will be understood, however, that the total daily usage of a formulation of the present disclosure will often be decided by the attending physician within the scope of sound medical judgment. In some embodiments, the specific effective dose level for any particular subject or organism may depend upon a variety of factors including the disorder being treated and the severity of the disorder; activity of specific active compound employed; specific composition employed; age, body weight, general health, sex and diet of the subject; time of administration, and rate of excretion of the specific active compound employed; duration of the treatment; drugs and/or additional therapies used in combination or coincidental with specific compound(s) employed, and like factors well known in the medical arts.

For purposes of this invention, the chemical elements are identified in accordance with the Periodic Table of the Elements, CAS version, Handbook of Chemistry and Physics, 67th Ed., 1986-87, inside cover.

DETAILED DESCRIPTION OF CERTAIN EMBODIMENTS

Without wishing to be bound by any particular theory, the present disclosure proposes that failure of memory in AD occurs at least in part because dopamine is not adequately provided as a result of the reduced number of LC axons in patients with AD. This insight suggests that methods for enhancing dopamine release from remaining LC axons may be therapeutic. As described herein, one target for treatment is dopamine-beta-hydroxylase (DBH), the enzyme that converts dopamine to noradrenaline.

Figure 1:
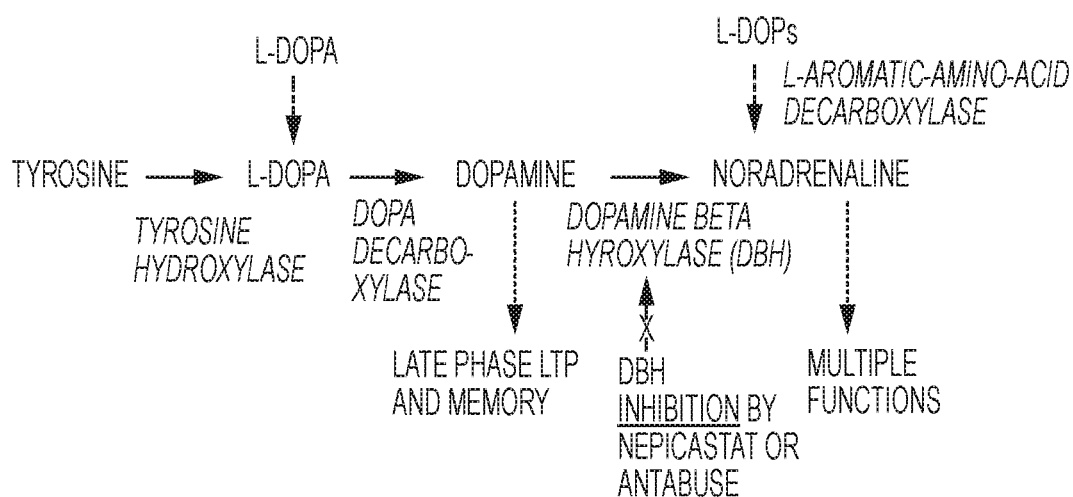
FIG. 1 depicts pathways involved in the synthesis of dopamine and noradrenaline.

For instance, in some embodiments, methods of the present invention contemplate enhancing dopamine release based on the biochemical pathways shown in FIG. 1. FIG. 1 depicts pathways involving the synthesis of noradrenaline via conversion of dopamine to noradrenaline by DBH. Accordingly, in some embodiments, the present invention provides methods of inhibiting DBH using, e.g., known DBH inhibitors disulfiram and Nepicastat. Disulfiram (sold under the trade name of Antabuse™) and Nepicastat (M Goldstein, Anagnoste, Lauber, & McKeregham, 1964; Stanley et al., 1997) are both well established DBH inhibitors that have been shown to increase the concentration of dopamine and/or increase dopamine release (Devoto et al., 2014; Menek Goldstein & Nakajima, 1967; Schroeder et al., 2010).

In some embodiments, present invention relates to the use of DBH inhibitors (e.g., disulfiram or Nepicastat) to treat or prevent certain types of memory loss, for instance memory loss associated with a neurodegenerative disease, disorder, or condition such as Alzheimer's disease. Without wishing to be bound by any particular theory, it is thought that DBH inhibitors (e.g., disulfiram or Nepicastat) increase the concentration of dopamine and/or increase dopamine release by inhibiting the conversion of dopamine to noradrenaline such that dopamine levels are increased.

One question in regard to this new strategy is whether the resulting decrease in noradrenaline will itself have bad consequences. Overall the data available do not provide a clear answer to this question. Available literature does not provide evidence of memory deficits produced by disulfiram. Consistent with this, it was shown that the DBH knockout does not affect AP levels in wt animals and causes only mild memory dysfunction in the Morris Water Maze (Hammerschmidt et al., 2013). Indeed another study showed that the minor deficits in the memory task are probably secondary to swimming deficits. (Thomas & Palmiter, 1997). On the other hand, experiments on LTP indicate that while noradrenaline is not necessary for late LTP, in can enhance LTP (Hopkins & Johnston, 1988). Furthermore, accelerated production of Aβ plaques occurs in the hippocampus as a result of LC degeneration (Gannon et al., 2015). Finally, evidence has been provided that β2-adrenergic agonist application is able to prevent damage that soluble Aβ oligomers have on LTP (Li et al., 2013). In summary, there is the real possibility there will be deleterious effects of reducing noradrenaline release by inhibiting DBH. Fortunately, the present disclosure also provides a likely solution; the human-approved drug (L-DOPS) increases levels of noradrenaline through a DBH-independent pathway, as shown in FIG. 1. Indeed this drug itself can have positive effects on Aβ pathology (Kalinin et al., 2012). Effects of DBH inhibition, with and without L-DOPS, can be assessed as described herein.

The present invention contemplates use of a DBH inhibitor (e.g., disulfiram or Nepicastat) in combination with one or more agents that ameliorate noradrenaline reduction potentially caused by and/or associated with DBH inhibitors. For instance, in some embodiments, the present invention contemplates use of a DBH inhibitor (e.g., disulfiram or Nepicastat) in combination with L-DOPS, also known as droxidopa, a drug approved for use in humans that increases levels of noradrenaline via a DBH-independent pathway.

Experiments with DBH inhibitors disulfiram and Nepicastat show that inhibitors of DBH raise dopamine levels. In accordance with the present disclosure, these inhibitors are assayed for their ability to enhance dopamine release and memory. The present disclosure describes using such agents alone and in combination with agents that ameliorate noradrenaline reduction potentially caused by DBH inhibitors, specifically L-DOPS, to increase dopamine release and/or memory, and/or to treat Alzheimer's disease.

Disulfiram

Disulfiram, i.e., 1,1',1",1"'-[disulfanediylbis(carbonothioylnitrilo)]tetraethane, is a non-selective DBH inhibitor historically used in the treatment of chronic alcoholism and/or cocaine addiction and is sold under the trade names Antabuse™ and Antabus™. Disulfiram works by inhibiting the enzyme acetaldehyde dehydrogenase, leading to a "hangover" feeling immediately after alcohol is consumed. In the body, alcohol is converted to actaldehyde, which is then broken down by aldehyde dehydrogenase. Inhibition of the dehydrogenase enzyme causes acetaldehyde build up, which leads to unpleasant effects. Disulfiram is also being studied as a treatment for cocaine dependence, as it prevents the breakdown of dopamine, a neurotransmitter whose release is stimulated by cocaine. Disulfiram is the subject of research for treatment of cancer and HIV (to activate the reservoir of HIV-infected resting CD4 cells).

In the context of treating chronic alcoholism, disulfiram may be administered according to an initial dose schedule of a maximum of about 500 mg daily, administered once a day in a single dose for one or two weeks, followed by a maintenance dose schedule of about 125 to 500 mg daily, the average maintenance dose being about 250 mg daily.

Nepicastat

Nepicastat, i.e., 5-(aminomethyl)-1-[(2S)-5,7-difluoro-1,2,3,4-tetrahydronaphthalen-2-yl]-1,3-dihydro-2H-imidazole-2-thione, was developed as a selective DBH inhibitor for treating PTSD and cocaine addiction. Nepicastat is not yet FDA approved but has been studied in clinical trials by Biotie Therapeutics Corp. Nepicastat has been used at up to 120 mg/day in phase 2 safety and efficacy studies for PTSD and cocaine addiction. This work indicates that in phase 1 safety studies, this dose was well tolerated. Nepicastat does not inhibit alcohol metabolism and may avoid undesirable side effects of disulfiram.

L-DOPS

L-DOPS, also known as droxidopa, i.e., (2S,3R)-2-Amino-3-(3,4-dihydroxyphenyl)-3-hydroxypropanoic acid, is an FDA approved synthetic amino acid precursor that acts as a prodrug to noradrenaline. L-DOPS is used in the treatment of neurogenic orthostatic hypotension (NOH) dopamine beta hydrolase deficiency, as well as NOH associated with multiple system atrophy (MSA), familial amyloid polyneuropathy (FAP), pure autonomic failure (PAF), intradialytic hypotension (IDH), hemodialysis-induced hypotension, and off label for treating the freezing of gait experienced by people suffering from Parkinson's Disease.

As described above, L-DOPS is a prodrug of noradrenaline used to increase the concentrations of these neurotransmitters in the body and brain. It is metabolized by aromatic L-amino acid decarboxylase (AAAD), also known as DOPA decarboxylase (DDC). Patients with NOH have depleted levels of noradrenaline which leads to decreased blood pressure or hypotension upon orthostatic challenge. L-DOPS works by increasing the levels of noradrenaline in the peripheral nervous system (PNS), thus enabling the body to maintain blood flow upon and while standing. L-DOPS can also cross the blood-brain barrier (BBB) where it is converted to noradrenaline from within the brain. Increased levels of noradrenaline in the central nervous system (CNS) may be beneficial to patients in a wide range of indications. L-DOPS can be coupled with a peripheral aromatic L-amino acid decarboxylase inhibitor (AAADI) or DOPA decarboxylase inhibitor (DDC) such as carbidopa (Lodosyn) to increase central noradrenaline concentrations while minimizing increases of peripheral levels. L-DOPS is currently initially administered orally (PO) in doses of 100 mg three times a day (TID). Dosing can be titrated to symptomatic response, in increments of 100 mg TID every 24-48 hr, usually not to exceed 600 mg TID (ie, 1800 mg/day).

Methods of Using DBH Inhibitors (e.g., Disulfiram or Nepicastat) in Accordance with the Present Invention The present invention encompasses the recognition that DBH inhibitors (e.g., disulfiram or Nepicastat) can be effective in treating or preventing certain types of memory loss, for instance memory loss associated with a neurodegenerative disease, disorder, or condition such as Alzheimer's disease. In some embodiments, the Alzheimer's disease is early stage Alzheimer's disease. Without wishing to be bound by any particular theory or mechanism of action, methods of the invention are useful in inhibiting the enzyme DBH from converting dopamine to noradrenaline. The invention provides methods for treating a subject suffering from or susceptible to certain types of memory loss, for instance memory loss associated with a neurodegenerative disease, disorder, or condition such as Alzheimer's disease, including the step of administering to the subject a therapeutically effective amount of a DBH inhibitor (e.g., disulfiram or Nepicastat), or a pharmaceutical composition thereof. In certain embodiments, the subject is a mouse or rat. In certain embodiments, the subject is an adult human. In some embodiments, the neurodegenerative disease, disorder, or condition is characterized by the occurrence of degeneration of the locus coeruleus (LC), for instance lesion formation. In certain embodiments, the neurodegenerative disease, disorder, or condition is Alzheimer's disease. In certain embodiments, the subject is an adult human undergoing treatment for Alzheimer's disease. Exemplary such treatments are known in the medical arts and contemplated herein for use in combination with the present invention.

Given the importance of dopaminergic modulation for late LTP, it was hypothesized that dopamine would also be important for memory itself. This was confirmed by Bethus et al. in 2010 (Bethus, Tse, & Morris, 2010), who demonstrated that the presence of a D1 antagonist in the hippocampus, while having little effect on learning or early memory, strongly reduces 1-day memory.

Until recently, it had generally been thought that dopamine release in the C1 hippocampal region occurs from the axons of the two midbrain dopaminergic structures, the ventral tegmental area (VTA) and substantia nigra (SN). Although classic anatomical labeling of dopamine axons did not reveal substantial innervation in the stratum radiatum of CA1 from these structures, the evidence was equivocal because of the vagaries of older methods (e.g., small axons don't label). However, with the advent of new labeling methods, there is now no doubt that the stratum radiatum of CA1 virtually lacks dopaminergic innervation (Mingote et al., 2012; Smith & Greene, 2012). Given that dopamine receptors are present in this region (Smith & Greene, 2012) and exert powerful effects on LTP and learning, this raised the question of where the dopamine was coming from.

Because the CA1 region is strongly innervated by noradrenergic axons from the locus coruleus (LC) (Moudy, Kunkel, & Schwartzkroin, 1993), one possibility was that these axons were the source of dopamine, which is the immediate precursor for noradrenaline (NA). This possibility was recently proven to be the case (Smith & Greene, 2012) in a study that used a known effect of dopamine, i.e., the longterm enhancement of the AMPAR-mediated EPSP by D1 agonist (Huang and Kandel, 1995), to monitor dopamine release. Molecular methods were used to inhibit dopamine synthesis in either the LC or VTA. The finding was that inhibition of dopamine synthesis in the LC blocked dopamine-dependent changes in CA1, whereas inhibiting the VTA had no effect. This conclusion has been strengthened by recent optogenetic work that used stimulation of channel-rhodopsin to excite axons of either the VTA or LC (Sonnebom et al., 2015). Stimulation of the LC terminals in hippocampal slices with light produced enhancement of late LTP, an effect that could be blocked by D1 antagonist. Moreover, the light-dependent release of dopamine from the LC was directly confirmed by HPLC (Sonnebom et al., 2015). In contrast, stimulation of the VTA axons had no effect. These results thus establish that functionally important dopamine is released from the noradrenergic axons of the LC.

This work has now been complemented by work showing the importance of LC-mediated dopamine release for memory itself (Takeuchi et al., 2015). Using channel-rhodopsin in the LC, it was demonstrated that light-induced activation of the LC has little effect on early memory (just as dopamine has little effect on early LTP), but strongly increases 1-day memory (consistent with dopamine enhancement of late LTP).

There is strong evidence for early and profound degeneration of the LC in Alzheimer's disease (Bondareff, Mountjoy, & Roth, 1982; Braak & Del Tredici, 2012). Of particular note was a study that specifically compared the degeneration in AD brain regions specialized for different neurotransmitters (dopamine, acetylcholine, noradrenaline, serotonin) (Zarow, Lyness, Mortimer, & Chui, 2003). This study showed that the region having the earliest and most severe degeneration is the LC.

Memory may be compromised in Alzheimer's disease, at least in the earlier stages, due to degeneration of the LC. Such degeneration of the LC may reduce dopamine release in the hippocampus and produce strong deficits in late LTP and long-term memory. One question that has been posed is whether the degeneration of the LC produces memory deficits that are independent of those produced by Aβ or whether these processes are synergistic. Data strongly indicate that synergism is at play (Hammerschmidt et al., 2013; Heneka, 2006; D. Jardanhazi-Kurutz et al., 2011; Daniel Jardanhazi-Kurutz et al., 2010; Oikawa, Ogino, Masumoto, Yamaguchi, & Yanagisawa, 2010). Studies have shown that degeneration of LC by DSP4, a toxin that selectively causes degeneration of LC axons (Ross & Stenfors, 2015), increases the production of Aβ plaques five-fold when APP mice are examined 6 months later (Kalinin et al., 2007).

Importantly, destruction of the LC in Alzheimer's disease is only partial; ~30% of LC axons remain (Marien, Colpaert, & Rosenquist, 2004; Szot et al., 2006). Thus, it is an object of the present invention to provide ways to restore LC function that may not only have immediate benefits for memory, but also slow Aβ pathology.

In some embodiments, the invention provides a method comprising steps of administering to a subject suffering from or susceptible to Alzheimer's disease an effective amount of a DBH inhibitor (e.g., disulfiram or Nepicastat), such that the severity or incidence of memory loss is reduced, or its onset is delayed. In some embodiments, a DBH inhibitor (e.g., disulfiram or Nepicastat) is administered in the form of a salt or pharmaceutically acceptable composition thereof. In certain embodiments, a DBH inhibitor (e.g., disulfiram or Nepicastat) is administered in accordance with the present invention to subjects suffering from or susceptible to memory loss, wherein the DBH inhibitor (e.g., disulfiram or Nepicastat) is administered in a form or composition and/or according to a known regimen established as useful in, e.g., the treatment of alcoholism, cocaine addiction, or PTSD, as discussed above. In some embodiments, a known regimen established as useful is a regimen that is used in the medical arts and/or has been approved by the FDA for the treatment of a particular indication, e.g., alcoholism, cocaine addiction, or PTSD. In certain embodiments, the subject is an adult human from about 40 to about 90 years of age.

In some embodiments, a DBH inhibitor (e.g., disulfiram or Nepicastat) is administered once a day. In some embodiments, a DBH inhibitor (e.g., disulfiram or Nepicastat) is administered two, three, four, or five times a day. In some embodiments, a DBH inhibitor (e.g., disulfiram or Nepicastat) is administered every other day. In some embodiments, a DBH inhibitor (e.g., disulfiram or Nepicastat) is administered every two days. In some embodiments, a DBH inhibitor (e.g., disulfiram or Nepicastat) is administered every three days. In some embodiments, a DBH inhibitor (e.g., disulfiram or Nepicastat) is administered every four days. In some embodiments, a DBH inhibitor (e.g., disulfiram or Nepicastat) is administered every five days. In some embodiments, a DBH inhibitor (e.g., disulfiram or Nepicastat) is administered every six days. In some embodiments, a DBH inhibitor (e.g., disulfiram or Nepicastat) is administered once a week. In some embodiments, a DBH inhibitor (e.g., disulfiram or Nepicastat) is administered at intervals as instructed by a physician for the duration of the life of the subject being treated. In certain embodiments, a DBH inhibitor (e.g., disulfiram or Nepicastat) is administered as many times a day as necessary to provide a therapeutically effective amount of a DBH inhibitor (e.g., disulfiram or Nepicastat) to treat a subject suffering from or susceptible to memory loss, for instance memory loss associated with a neurodegenerative disease, disorder, or condition such as Alzheimer's disease.

In some embodiments, a DBH inhibitor is disulfiram. In some embodiments, disulfiram is administered in a form or composition and/or according to a regimen established as useful in the treatment of any of the above-described diseases, disorders, or conditions for which disulfiram is used and/or approved to treat. In some embodiments, disulfiram is used in combination with L-DOPS. In some such embodiments, L-DOPS is administered in a form or composition and/or according to a known regimen established as useful in the treatment of any of the above-described diseases, disorders, or conditions for which L-DOPS is used and/or approved to treat.

In some embodiments, a DBH inhibitor is Nepicastat. In some embodiments, Nepicastat is administered in a form or composition and/or according to a regimen established as useful in any of the above-described diseases, disorders, or conditions for which Nepicastat is used and/or approved to treat. In some embodiments, Nepicastat is used in combination with L-DOPS. In some such embodiments, L-DOPS is administered in a form or composition and/or according to a known regimen established as useful in the treatment of any of the above-described diseases, disorders, or conditions for which L-DOPS is used and/or approved to treat.

In some embodiments, a subject suffering from or susceptible to certain types of memory loss, for instance memory loss associated with a neurodegenerative disease, disorder, or condition such as Alzheimer's disease, is a mammal. In some such embodiments, the subject is a rodent, such as a rat or mouse, for example, an AD model rat or mouse. In some embodiments, the subject is an adult human. In certain embodiments, the adult human is about 40, 60, 70, 80, 90, or 100 years of age. In certain embodiments, the adult human is between 40 and 85 years of age.

The efficacy of a DBH inhibitor (e.g., disulfiram or Nepicastat) used in accordance with the present invention may be evaluated and/or followed using any method known in the medical arts. For instance, in some embodiments, evaluation comprises testing the memory of a subject being treated with a DBH inhibitor. In some embodiments, evaluation comprises monitoring the subject being treated with a DBH inhibitor. In some embodiments, the subject is monitored by monitoring behavior. In some embodiments, the subject is evaluated or monitored one, two, three, four, or five times a day. In some embodiments, the subject is evaluated or monitored one, two, three, four or five times a week. In some embodiments, the subject is evaluated or monitored twice a week. In some embodiments, monitoring is continuous. In some embodiments, monitoring occurs for the duration of the subject's life. In certain embodiments, the subject is monitored one, two, or three times a day by monitoring behavior. In some embodiments, the subject is a human and is monitored using any of the methods known in the medical arts suitable for monitoring humans suffering from or susceptible to certain types of memory loss, for instance memory loss associated with a neurodegenerative disease, disorder, or condition such as Alzheimer's disease. In some embodiments, monitoring may comprise checking for signs of toxicity associated with a DBH inhibitor. In certain embodiments, the DBH inhibitor is disulfiram or Nepacastat and toxicity is measured using any of the methods previously developed to measure toxicity of disulfiram or Nepcastat, for instance when used to treat patients for chronic alcoholism and/or cocaine abuse. Such methods of evaluating efficacy and/or toxicity are known in the medical arts and contemplated herein.

Dosages of a DBH inhibitor (e.g., disulfiram or Nepcastat) utilized in accordance with the present invention may vary with the form of administration and/or with the particular subject being treated. In general, a DBH inhibitor (e.g., disulfiram or Nepcastat) is most desirably administered at a concentration level that will afford effective results without causing any harmful or deleterious side-effects. In some embodiments, a DBH inhibitor (e.g., disulfiram or Nepcastat) is administered in doses ranging from about 0.5 to about 500 mg/kg/day. In some embodiments, a DBH inhibitor (e.g., disulfiram or Nepcastat) is administered in doses ranging from about 0.5 to about 100 mg/kg/day. In some embodiments, a DBH inhibitor (e.g., disulfiram or Nepcastat) is administered in doses ranging from about 0.5 to about 90 mg/kg/day. In some embodiments, a DBH inhibitor (e.g., disulfiram or Nepcastat) is administered in doses ranging from about 0.5 to about 80 mg/kg/day. In some embodiments, a DBH inhibitor (e.g., disulfiram or Nepcastat) is administered in doses ranging from about 0.5 to about 70 mg/kg/day. In some embodiments, a DBH inhibitor (e.g., disulfiram or Nepcastat) is administered in doses ranging from about 1 to about 60 mg/kg/day. In some embodiments, a DBH inhibitor (e.g., disulfiram or Nepcastat) is administered in doses ranging from about 1 to about 50 mg/kg/day. In some embodiments, a DBH inhibitor (e.g., disulfiram or Nepcastat) is administered in doses ranging from about 1 to about 40 mg/kg/day. In some embodiments, a DBH inhibitor (e.g., disulfiram or Nepcastat) is administered in doses ranging from about 1 to about 30 mg/kg/day. In some embodiments, a DBH inhibitor (e.g., disulfiram or Nepcastat) is administered in doses ranging from about 1 to about 20 mg/kg/day. In some embodiments, a DBH inhibitor (e.g., disulfiram or Nepcastat) is administered in doses ranging from about 1 to about 10 mg/kg/day. In some embodiments, a DBH inhibitor (e.g., disulfiram or Nepcastat) is administered in doses of less than about 20 mg/kg/day. In some embodiments, a DBH inhibitor (e.g., disulfiram or Nepcastat) is administered in doses ranging from about 1 mg/kg/day to about 8 mg/kg/day. In some embodiments, a DBH inhibitor (e.g., disulfiram or Nepcastat) is administered in doses ranging from about 1 mg/kg/day to about 7 mg/kg/day. In some embodiments, a DBH inhibitor (e.g., disulfiram or Nepcastat) is administered in doses ranging from about 1 mg/kg to about 6 mg/kg/day.

In some embodiments, a DBH inhibitor (e.g., disulfiram or Nepcastat) is administered in doses ranging from about 1 mg/kg/day to about 5 mg/kg/day. In some embodiments, a DBH inhibitor (e.g., disulfiram or Nepcastat) is administered in doses ranging from about 1 mg/kg/day to about 4 mg/kg/day. In some embodiments, a DBH inhibitor (e.g., disulfiram or Nepcastat) is administered in doses ranging from about 1 mg/kg/day to about 3 mg/kg/day. In some embodiments, a DBH inhibitor (e.g., disulfiram or Nepcastat) is administered in doses ranging from about 1 mg/kg/day to about 2 mg/kg/day. In some embodiments, a DBH inhibitor (e.g., disulfiram or Nepcastat) is administered in doses less than about 10 mg/kg/day. In some embodiments, a DBH inhibitor (e.g., disulfiram or Nepcastat) is administered in doses less than about 5 mg/kg/day. In some embodiments, a DBH inhibitor (e.g., disulfiram or Nepcastat) is administered in doses less than about 4 mg/kg/day. In some embodiments, a DBH inhibitor (e.g., disulfiram or Nepcastat) is administered in doses less than about 3 mg/kg/day. In some embodiments, a DBH inhibitor (e.g., disulfiram or Nepcastat) is administered in doses less than about 2 mg/kg/day. In some embodiments, a DBH inhibitor (e.g., disulfiram or Nepcastat) is administered in doses less than about 1 mg/kg/day. In some embodiments, a DBH inhibitor (e.g., disulfiram or Nepcastat) is administered in doses less than about 0.5 mg/kg/day. In some embodiments, a DBH inhibitor (e.g., disulfiram or Nepcastat) is administered in doses of about 0.1, 0.2, 0.3, 0.4, 0.5, 0.6, 0.7, 0.8, 0.9, or 1.0 mg/kg/day. In some embodiments, a DBH inhibitor (e.g., disulfiram or Nepcastat) is administered in doses of about 1, 2, 3, 4, 5, 6, 7, 8, or 9 mg/kg/day. In some embodiments, a DBH inhibitor (e.g., disulfiram or Nepcastat) is administered in doses ranging from about 0.1 mg/kg/day to about 5 mg/kg/day. In some embodiments, a DBH inhibitor (e.g., disulfiram or Nepcastat) is administered in doses of about 1 mg/kg/day. In some embodiments, a DBH inhibitor (e.g., disulfiram or Nepcastat) is administered in doses of about 2 mg/kg/day. In some embodiments, a DBH inhibitor (e.g., disulfiram or Nepcastat) is administered in doses of about 3 mg/kg/day. In some embodiments, a DBH inhibitor (e.g., disulfiram or Nepcastat) is administered in doses of about 4 mg/kg/day. In some embodiments, a DBH inhibitor (e.g., disulfiram or Nepcastat) is administered in doses of about 5 mg/kg/day. In some embodiments, a DBH inhibitor (e.g., disulfiram or Nepcastat) is administered in doses of about 6 mg/kg/day.

In some embodiments, a DBH inhibitor (e.g., disulfiram or Nepcastat) is administered in doses ranging from about 10 mg/kg/day to about 200 mg/kg/day. In some embodiments, a DBH inhibitor (e.g., disulfiram or Nepcastat) is administered in doses ranging from about 20 mg/kg/day to about 190 mg/kg/day. In some embodiments, a DBH inhibitor (e.g., disulfiram or Nepcastat) is administered in doses ranging from about 20 mg/kg/day to about 180 mg/kg/day. In some embodiments, a DBH inhibitor (e.g., disulfiram or Nepcastat) is administered in doses ranging from about 20 mg/kg/day to about 170 mg/kg/day. In some embodiments, a DBH inhibitor (e.g., disulfiram or Nepcastat) is administered in doses ranging from about 20 mg/kg/day to about 160 mg/kg/day. In some embodiments, a DBH inhibitor (e.g., disulfiram or Nepcastat) is administered in doses ranging from about 20 mg/kg/day to about 150 mg/kg/day. In some embodiments, a DBH inhibitor (e.g., disulfiram or Nepcastat) is administered in doses ranging from about 20 mg/kg/day to about 140 mg/kg/day. In some embodiments, a DBH inhibitor (e.g., disulfiram or Nepcastat) is administered in doses ranging from about 20 mg/kg/day to about 130 mg/kg/day. In some embodiments, a DBH inhibitor (e.g., disulfiram or Nepcastat) is administered in doses ranging from about 20 mg/kg/day to about 120 mg/kg/day. In some embodiments, a DBH inhibitor (e.g., disulfiram or Nepcastat) is administered in doses ranging from about 20 mg/kg/day to about 110 mg/kg/day. In some embodiments, a DBH inhibitor (e.g., disulfiram or Nepcastat) is administered in doses ranging from about 20 mg/kg/day to about 100 mg/kg/day. In some embodiments, a DBH inhibitor (e.g., disulfiram or Nepcastat) is administered in doses ranging from about 30 mg/kg/day to about 90 mg/kg/day. In some embodiments, a DBH inhibitor (e.g., disulfiram or Nepcastat) is administered in doses ranging about 25 mg/kg/day to about 75 mg/kg/day. In some embodiments, a DBH inhibitor (e.g., disulfiram or Nepcastat) is administered in doses ranging about 25 mg/kg/day to about 50 mg/kg/day. In some embodiments, a DBH inhibitor (e.g., disulfiram or Nepcastat) is administered in doses of about 50 mg/kg/day. In some embodiments, a DBH inhibitor (e.g., disulfiram or Nepcastat) is administered in doses of about 100 mg/kg/day.

In some embodiments, a DBH inhibitor (e.g., disulfiram or Nepcastat) is administered systemically in any one of the doses described herein and/or suitable for the treatment of certain types of memory loss, for instance memory loss associated with a neurodegenerative disease, disorder, or condition such as Alzheimer's disease. Systemic administration may comprise enteral or parenteral administration. In certain embodiments, systemic administration comprises oral administration in solid or solution form in any one of the doses described herein. In certain embodiments, a DBH inhibitor is disulfiram or Nepcastat and is administered orally in any one of the doses described herein and/or known in the medical arts for treating a particular indication, and/or approved for use in treating a particular indication (e.g., chronic alcoholism and/or cocaine addiction). In some embodiments, a DBH inhibitor (e.g., disulfiram or Nepcastat) is administered orally and the subject is an adult human suffering from or susceptible to Alzheimer's disease. In certain embodiments, a DBH inhibitor (e.g., disulfiram or Nepcastat) is administered intraperitoneally in any one of the doses described herein and the subject is an AD model mouse or rat.

As described above and herein, the present invention contemplates methods of treatment further comprising administering to a subject in need thereof an amount of a one or more agents that ameliorate noradrenaline reduction associated with use of a DBH inhibitor, for instance L-DOPS. Dosages of such an agent, for instance L-DOPS, utilized in accordance with the present invention may vary with the form of administration and/or with the particular subject being treated. In general, such an agent, for instance L-DOPS, is most desirably administered at a concentration level that will afford effective results without causing any harmful or deleterious side-effects. In some embodiments, such an agent is administered in doses ranging from about 0.5 to about 500 mg/kg/day. In some embodiments such an agent is administered in doses ranging from about 0.5 to about 100 mg/kg/day. In some embodiments, such an agent is administered in doses ranging from about 0.5 to about 90 mg/kg/day. In some embodiments, such an agent is administered in doses ranging from about 0.5 to about 80 mg/kg/day. In some embodiments, such an agent is administered in doses ranging from about 0.5 to about 70 mg/kg/day. In some embodiments, such an agent is administered in doses ranging from about 1 to about 60 mg/kg/day. In some embodiments, such an agent is administered in doses ranging from about 1 to about 50 mg/kg/day. In some embodiments, such an agent is administered in doses ranging from about 1 to about 40 mg/kg/day. In some embodiments, such an agent is administered in doses ranging from about 1 to about 30 mg/kg/day. In some embodiments, such an agent is administered in doses ranging from about 1 to about 20 mg/kg/day. In some embodiments, such an agent is administered in doses ranging from about 1 to about 10 mg/kg/day. In some embodiments, such an agent is administered in doses of less than about 20 mg/kg/day.

In some embodiments, the one or more agents that ameliorate noradrenaline reduction associated with use of a DBH inhibitor is or comprises L-DOPS, administered in any one of the doses described herein and/or known in the medical arts and/or approved for treating a particular indication (e.g., neurogenic orthostatic hypotension (NOH)). For instance, in some embodiments, L-DOPS is administered three times daily (TD). In some such embodiments, L-DOPS is titrated to symptomatic response. In some embodiments, L-DOPS is administered at an initial dose of about 50 mg to about 200 mg (TID). In some embodiments, L-DOPS is administered at increasing doses up to about 2500 mg/day. In some embodiments, a total daily dose of L-DOPS is from about 150 mg to about 2500 mg. In some embodiments, a total daily dose of L-DOPS is about 150 mg, 200 mg, 250 mg, 300 mg, 350 mg, 400 mg, 450 mg, 500 mg, 550 mg, 600 mg, 650 mg, 700 mg, 750 mg, 800 mg, 850 mg, 900 mg, 950 mg, 1000 mg, 1050 mg, 1100 mg, 1150 mg, 1200 mg, 1250 mg, 1300 mg, 1350 mg, 1400 mg, 1450 mg, 1500 mg, 1550 mg, 1600 mg, 1650 mg, 1700 mg, 1750 mg, 1800 mg, 1850 mg, 1900 mg, 1950 mg, 2000 mg, 2050 mg, 2100 mg, 2150 mg, 2200 mg, 2250 mg, 2300 mg, 2350 mg, 2400 mg, 2450 mg, or 2500 mg.

In some embodiments, the invention provides methods comprising steps of administering to a subject suffering from or susceptible to certain types of memory loss, for instance memory loss associated with a neurodegenerative disease, disorder, or condition such as Alzheimer's disease, an amount of a DBH inhibitor (e.g., disulfiram or Nepcastat) sufficient to reduce or delay such memory loss.

In some embodiments, the invention provides methods comprising steps of administering to a subject suffering from or susceptible to amyloid beta plaques associated with Alzheimer's disease an amount of a DBH inhibitor (e.g., disulfiram or Nepcastat) sufficient to reduce or delay the formation of such plaques. In some embodiments, the subject is a mammal. In some embodiments, the subject is an AD model mouse or rat. In some embodiments, the subject is an adult human. In certain embodiments, the adult human is about 40, 50, 60, 70, 80, 90, or 100 years of age.

In some embodiments, a DBH inhibitor (e.g., disulfiram or Nepcastat) is administered to a subject with a Alzheimer's disease using any method of administration known in the medical arts. In certain embodiments, a DBH inhibitor (e.g., disulfiram or Nepcastat) may be administered orally. In certain embodiments, a DBH inhibitor (e.g., disulfiram or Nepcastat) may be administered parenterally. In certain embodiments, a DBH inhibitor (e.g., disulfiram or Nepcastat) is administered intraperitoneally.

In some embodiments, the present invention provides systems, methods, and/or reagents to characterize DBH inhibitors and/or compositions thereof. In some embodiments, the present invention provides assays to identify DBH inhibitors capable of treating or preventing certain types of memory loss, for instance memory loss associated with a neurodegenerative disease, disorder, or condition such as Alzheimer's disease. In some embodiments, the present invention provides assays to identify DBH inhibitors capable of increasing levels of dopamine in the LC. In some embodiments, the present invention provides assays to identify DBH inhibitors capable of reducing or delaying the formation of amyloid beta plaques.

DBH inhibitors and compositions identified using the above-mentioned assays may be further examined using biological assays to guide structure-activity relationship (SAR) analyses of the identified compounds. Biological assays and SAR analyses are known to those of skill in the art.

Combination Therapies

As described above and herein, in some embodiments, compositions and methods of the present invention are used in combination therapies. For instance, DBH inhibitors (e.g., disulfiram or Nepicastat) used in accordance with the present invention can be administered concurrently with, prior to, or subsequent to, one or more other desired therapeutic agents or medical procedures. The particular combination of therapies (therapeutic agents or procedures) to employ in a combination regimen will take into account compatibility of the desired therapeutic agents and/or procedures and the desired therapeutic effect to be achieved. It will also be appreciated that the therapies employed may achieve a desired effect for the same disorder (for example, a compound described herein may be administered concurrently with another therapeutic agent used to treat the same disorder), or they may achieve different effects (e.g., control of any adverse effects).

For example, known agents useful for treating neurodegenerative diseases, disorders, or conditions may be combined with compositions and methods of the present invention to treat neurodegenerative diseases, disorders, or conditions, such as Alzheimer's disease. Examples of such known agents include, but are not limited to, acetylcholinesterase inhibitors, including donepezil, Exelon® and others; memantine (and related compounds as NMDA inhibitors), treatments for Parkinson's disease such as L-DOPA/carbidopa, entacapone, ropinrole, pramipexole, bromocriptine, pergolide, trihexephendyl, and amantadine; agents for treating Multiple Sclerosis (MS) such as beta interferon (e.g., Avonex® and Rebif®), Copaxone®, and mitoxantrone; riluzole, and anti-Parkinsonian agents. For a more comprehensive discussion of updated therapies useful for treating neurodegenerative disorders, see, a list of the FDA approved drugs at http://www.fda.gov, and The Merck Manual, Seventeenth Ed. 1999, the entire contents of which are hereby incorporated by reference.

Additional examples of such known agents useful for treating neurodegenerative diseases, disorders, or conditions include, but are not limited to, beta-secretase inhibitors/modulators, catechol-O-methyl transferase (COMT) inhibitors, dopamine reuptake inhibitors, gamma-secretase inhibitors/modulators, HMG-CoA reductase inhibitors, NSAID's including ibuprofen, vitamin E, anti-amyloid antibodies, including humanized monoclonal antibodies, inhibitors/modulators of tau phosphorylation (such as GSK3 or CDK inhibitors/modulators) and/or aggregation, CB-1 receptor antagonists or CB-1 receptor inverse agonists, antibiotics such as doxycycline and rifampin, N-methyl-D-aspartate (NMDA) receptor antagonists, such as mematine, cholinesterase inhibitors such as galantamine, rivastigmnine, donepezil and tacrine, growth hormone secretagogues such as ibutamoren, ibutamoren mesylate and capromorelin, histamine $H_3$ antagonists, AMPA agonists, PDE-IV, -V, -VII, -VIII, and -IX inhibitors, $GABA_A$ inverse agonists, and neuronal nicotinic agonists and partial agonists, serotonin receptor antagonists.

In some embodiments, compositions and methods of the present invention are combined with a dopamine reuptake inhibitor selected from altropane (O-587), amfonelic acid (WIN 25978), aminaptine, BTCP (GK-13), DBL-583, difluoropine (O-620), GBR-12783, GBR-12935, GBR-13069. GBR-13098, GYKI-52895, lometopane (beta-CIT, RTI-55), methylphenidate, RTI-229, and vanoxerine (GBR-12909).

In some embodiments, compositions and methods of the present invention are combined with a dopamine reuptake inhibitor selected from chaenomeles speciose (Flowering Quince), Oroxylin A, Kavain, and desmethoxyangonin.

In some embodiments, compositions and methods of the present invention are combined with a dopamine reuptake inhibitor selected from adrafinil, armodafinil, benztropine, buproprion, fluorenol, medifoxamine, metaphit, modafinil, rimcazole, and venlafaxine.

In some embodiments, compositions and methods of the present invention are combined with a catechol-O-methyl transferase (COMT) inhibitor selected from entacapone, tolcapone, and nitecapone.

In some embodiments, compositions and methods of the present invention are combined with other agents useful for treating neurodegenerative diseases, disorders, or conditions such as Alzheimer's disease, wherein such agents include beta-secretase inhibitors/modulators, gamma-secretase inhibitors/modulators, anti-amyloid antibodies, including humanized monoclonal antibodies aggregation inhibitors, metal chelators, antioxidants, and neuroprotectants and inhibitors/modulators of tau phosphorylation (such as GSK3 or CDK inhibitors/modulators) and/or aggregation.

In some embodiments, compositions and methods of the present invention are combined with gamma secretase modulators. In some embodiments, compounds of the present invention are gamma secretase modulators combined with gamma secretase modulators. Exemplary such gamma secretase modulators include, inter alia, certain NSAIDs and their analogs (see WO01/78721 and US 2002/0128319 and Weggen et al., Nature, 414 (2001) 212-16; Morihara et al., J. Neurochem., 83 (2002), 1009-12; and Takahashi et al., J. Biol. Chem., 278 (2003), 18644-70).

Pharmaceutical Compositions

In some embodiments, the present invention provides pharmaceutical compositions, which comprise a therapeutically effective amount of a DBH inhibitor (e.g., disulfiram or Nepicastat), formulated together with one or more pharmaceutically acceptable carriers (additives) and/or diluents. As described in detail, the pharmaceutical compositions of the present invention may be specially formulated for administration in solid or liquid form, including those adapted for the following: oral administration, for example, drenches (aqueous or non-aqueous solutions or suspensions), tablets, e.g., those targeted for buccal, sublingual, and systemic absorption, boluses, powders, granules, pastes for application to the tongue; parenteral administration, for example, by subcutaneous, intramuscular, intravenous or epidural injection as, for example, a sterile solution or suspension, or sustained-release formulation; topical application, for example, as a cream, ointment, or a controlled-release patch or spray applied to the skin, lungs, or oral cavity; intravaginally or intrarectally, for example, as a pessary, cream or foam; sublingually; ocularly; transdermally; or nasally, pulmonary and to other mucosal surfaces.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

In another aspect, the present invention provides "pharmaceutically acceptable" compositions, which comprise a therapeutically effective amount of one or more of the compounds described herein, formulated together with one or more pharmaceutically acceptable carriers (additives) and/or diluents. As described in detail, the pharmaceutical compositions of the present invention may be specially formulated for administration in solid or liquid form, including those adapted for the following: oral administration, for example, drenches (aqueous or non-aqueous solutions or suspensions), tablets, e.g., those targeted for buccal, sublingual, and systemic absorption, boluses, powders, granules, pastes for application to the tongue; parenteral administration, for example, by subcutaneous, intramuscular, intravenous or epidural injection as, for example, a sterile solution or suspension, or sustained-release formulation; topical application, for example, as a cream, ointment, or a controlled-release patch or spray applied to the skin, lungs, or oral cavity; intravaginally or intrarectally, for example, as a pessary, cream or foam; sublingually; ocularly; transdermally; or nasally, pulmonary and to other mucosal surfaces.

The phrase "pharmaceutically acceptable carrier" as used herein means a pharmaceutically acceptable material, composition or vehicle, such as a liquid or solid filler, diluent, excipient, or solvent encapsulating material, involved in carrying or transporting the subject compound from one organ, or portion of the body, to another organ, or portion of the body. Each carrier should be "acceptable" in the sense of being compatible with the other ingredients of the formulation and not injurious to the patient. Some examples of materials which can serve as pharmaceutically acceptable carriers include: sugars, such as lactose, glucose and sucrose; starches, such as corn starch and potato starch; cellulose, and its derivatives, such as sodium carboxymethyl cellulose, ethyl cellulose and cellulose acetate; powdered tragacanth; malt; gelatin; talc; excipients, such as cocoa butter and suppository waxes; oils, such as peanut oil, cottonseed oil, safflower oil, sesame oil, olive oil, corn oil and soybean oil; glycols, such as propylene glycol; polyols, such as glycerin, sorbitol, mannitol and polyethylene glycol; esters, such as ethyl oleate and ethyl laurate; agar; buffering agents, such as magnesium hydroxide and aluminum hydroxide; alginic acid; pyrogen-free water; isotonic saline; Ringer's solution; ethyl alcohol; pH buffered solutions; polyesters, polycarbonates and/or polyanhydrides; and other non-toxic compatible substances employed in pharmaceutical formulations.

In some embodiments, a DBH inhibitor (e.g., disulfiram or Nepicastat) for use in accordance with the present invention is provided in a salt form. Such salts can be prepared in situ in the administration vehicle or the dosage form manufacturing process, or by separately reacting a purified compound of the invention in its free base form with a suitable organic or inorganic acid, and isolating the salt thus formed during subsequent purification. Representative salts include salts such as the sulfate, phosphate, lactate, tartrate, maleate, citrate, hydrochloride (Bruderlein et al., U.S. Pat. No. 3,657, 250) and the like. See also, for example, Berge et al. (1977) "Pharmaceutical Salts", J. Pharm. Sci. 66:1-19; incorporated herein by reference.

Wetting agents, emulsifiers and lubricants, such as sodium lauryl sulfate and magnesium stearate, as well as coloring agents, release agents, coating agents, sweetening, flavoring and perfuming agents, preservatives and antioxidants can also be present in the compositions.

Examples of pharmaceutically acceptable antioxidants include: water soluble antioxidants, such as ascorbic acid, cysteine hydrochloride, sodium bisulfate, sodium metabisulfite, sodium sulfite and the like; oil-soluble antioxidants, such as ascorbyl palmitate, butylated hydroxyanisole (BHA), butylated hydroxytoluene (BHT), lecithin, propyl gallate, alpha-tocopherol, and the like; and metal chelating agents, such as citric acid, ethylenediamine tetraacetic acid (EDTA), sorbitol, tartaric acid, phosphoric acid, and the like.

Formulations of the present invention include those suitable for oral, nasal, topical (including buccal and sublingual), rectal, vaginal and/or parenteral administration. The formulations may conveniently be presented in unit dosage form and may be prepared by any methods well known in the art of pharmacy. The amount of active ingredient which can be combined with a carrier material to produce a single dosage form will vary depending upon the host being treated, and the particular mode of administration. The amount of active ingredient that can be combined with a carrier material to produce a single dosage form will generally be that amount of a DBH inhibitor (e.g., disulfiram or Nepicastat) which produces a therapeutic effect. Generally, this amount will range from about 1% to about 99% of active ingredient, preferably from about 5% to about 70%, most preferably from about 10% to about 30%.

In certain embodiments, a formulation of the present invention comprises an excipient selected from the group consisting of cyclodextrins, liposomes, micelle forming agents, e.g., bile acids, and polymeric carriers, e.g., polyesters and polyanhydrides; and a compound of the present invention. In certain embodiments, an aforementioned formulation renders orally bioavailable a compound of the present invention.

Methods of preparing these formulations or compositions include the step of bringing into association a compound of the present invention with the carrier and, optionally, one or more accessory ingredients. In general, the formulations are prepared by uniformly and intimately bringing into association a compound of the present invention with liquid carriers, or finely divided solid carriers, or both, and then, if necessary, shaping the product.

Formulations of the invention suitable for oral administration may be in the form of capsules, cachets, pills, tablets, lozenges (using a flavored basis, usually sucrose and acacia or tragacanth), powders, granules, or as a solution or a suspension in an aqueous or non-aqueous liquid, or as an oil-in-water or water-in-oil liquid emulsion, or as an elixir or syrup, or as pastilles (using an inert base, such as gelatin and glycerin, or sucrose and acacia) and/or as mouth washes and the like, each containing a predetermined amount of a compound of the present invention as an active ingredient. A compound of the present invention may also be administered as a bolus, electuary or paste.

In solid dosage forms of the invention for oral administration (capsules, tablets, pills, dragees, powders, granules and the like), the active ingredient is mixed with one or more pharmaceutically-acceptable carriers, such as sodium citrate or dicalcium phosphate, and/or any of the following: fillers or extenders, such as starches, lactose, sucrose, glucose, mannitol, and/or silicic acid; binders, such as, for example, carboxymethylcellulose, alginates, gelatin, polyvinyl pyrrolidone, sucrose and/or acacia; humectants, such as glycerol; disintegrating agents, such as agar-agar, calcium carbonate, potato or tapioca starch, alginic acid, certain silicates, and sodium carbonate; solution retarding agents, such as paraffin; absorption accelerators, such as quaternary ammonium compounds; wetting agents, such as, for example, cetyl alcohol, glycerol monostearate, and nonionic surfactants; absorbents, such as kaolin and bentonite clay; lubricants, such as talc, calcium stearate, magnesium stearate, solid polyethylene glycols, sodium lauryl sulfate, and mixtures thereof; and coloring agents. In the case of capsules, tablets and pills, the pharmaceutical compositions may also comprise buffering agents. Solid compositions of a similar type may also be employed as fillers in soft and hard-shelled gelatin capsules using such excipients as lactose or milk sugars, as well as high molecular weight polyethylene glycols and the like.

A tablet may be made by compression or molding, optionally with one or more accessory ingredients. Compressed tablets may be prepared using binder (for example, gelatin or hydroxypropylmethyl cellulose), lubricant, inert diluent, preservative, disintegrant (for example, sodium starch glycolate or cross-linked sodium carboxymethyl cellulose), surface-active or dispersing agent. Molded tablets may be made in a suitable machine in which a mixture of the powdered compound is moistened with an inert liquid diluent.

Tablets, and other solid dosage forms of the pharmaceutical compositions of the present invention, such as dragees, capsules, pills and granules, may optionally be scored or prepared with coatings and shells, such as enteric coatings and other coatings well known in the pharmaceutical-formulating art. They may also be formulated so as to provide slow or controlled release of the active ingredient therein using, for example, hydroxypropylmethyl cellulose in varying proportions to provide the desired release profile, other polymer matrices, liposomes and/or microspheres. They may be formulated for rapid release, e.g., freeze-dried. They may be sterilized by, for example, filtration through a bacteria-retaining filter, or by incorporating sterilizing agents in the form of sterile solid compositions that can be dissolved in sterile water, or some other sterile injectable medium immediately before use. These compositions may also optionally contain opacifying agents and may be of a composition that they release the active ingredient(s) only, or preferentially, in a certain portion of the gastrointestinal tract, optionally, in a delayed manner. Examples of embedding compositions that can be used include polymeric substances and waxes. The active ingredient can also be in micro-encapsulated form, if appropriate, with one or more of the above-described excipients.

Liquid dosage forms for oral administration of a DBH inhibitor (e.g., disulfiram or Nepicastat) of the invention include pharmaceutically acceptable emulsions, microemulsions, solutions, suspensions, syrups and elixirs. In addition to the active ingredient, the liquid dosage forms may contain inert diluents commonly used in the art, such as, for example, water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor and sesame oils), glycerol, tetrahydrofuryl alcohol, polyethylene glycols and fatty acid esters of sorbitan, and mixtures thereof.

Besides inert diluents, the oral compositions can also include adjuvants such as wetting agents, emulsifying and suspending agents, sweetening, flavoring, coloring, perfuming and preservative agents.

Suspensions, in addition to the active compound, may contain suspending agents as, for example, ethoxylated isostearyl alcohols, polyoxyethylene sorbitol and sorbitan esters, microcrystalline cellulose, aluminum metahydroxide, bentonite, agar-agar and tragacanth, and mixtures thereof.

Formulations of the pharmaceutical compositions of the invention for rectal or vaginal administration may be presented as a suppository, which may be prepared by mixing one or more compounds of the invention with one or more suitable nonirritating excipients or carriers comprising, for example, cocoa butter, polyethylene glycol, a suppository wax or a salicylate, and which is solid at room temperature, but liquid at body temperature and, therefore, will melt in the rectum or vaginal cavity and release the active compound.

Dosage forms for the topical or transdermal administration of a DBH inhibitor (e.g., disulfiram or Nepicastat) include powders, sprays, ointments, pastes, creams, lotions, gels, solutions, patches and inhalants. The DBH inhibitor (e.g., disulfiram or Nepicastat) may be mixed under sterile conditions with a pharmaceutically-acceptable carrier, and with any preservatives, buffers, or propellants which may be required.

The ointments, pastes, creams and gels may contain, in addition to a DBH inhibitor (e.g., disulfiram or Nepicastat), excipients, such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to a DBH inhibitor (e.g., disulfiram or Nepicastat), excipients such as lactose, talc, silicic acid, aluminum hydroxide, calcium silicates and polyamide powder, or mixtures of these substances. Sprays can additionally contain customary propellants, such as chlorofluorohydrocarbons and volatile unsubstituted hydrocarbons, such as butane and propane.

Transdermal patches may have the added advantage of providing controlled delivery of a DBH inhibitor (e.g., disulfiram or Nepicastat) to the body. Dissolving or dispersing a DBH inhibitor (e.g., disulfiram or Nepicastat) in the proper medium can make such dosage forms. Absorption enhancers can also be used to increase the flux of a DBH inhibitor (e.g., disulfiram or Nepicastat) across the skin. Either providing a rate controlling membrane or dispersing a DBH inhibitor (e.g., disulfiram or Nepicastat) in a polymer matrix or gel can control the rate of such flux.

Ophthalmic formulations, eye ointments, powders, solutions and the like, are also contemplated as being within the scope of this invention.

Pharmaceutical compositions of this invention suitable for parenteral administration comprise a DBH inhibitor (e.g., disulfiram or Nepicastat) in combination with one or more pharmaceutically-acceptable sterile isotonic aqueous or nonaqueous solutions, dispersions, suspensions or emulsions, or sterile powders which may be reconstituted into sterile injectable solutions or dispersions just prior to use, which may contain sugars, alcohols, antioxidants, buffers, bacteriostats, solutes which render the formulation isotonic with the blood of the intended recipient or suspending or thickening agents.

Examples of suitable aqueous and nonaqueous carriers, which may be employed in the pharmaceutical compositions of the invention include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

These compositions may also contain adjuvants such as preservatives, wetting agents, emulsifying agents and dispersing agents. Prevention of the action of microorganisms upon the a DBH inhibitor (e.g., disulfiram or Nepicastat) may be ensured by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents which delay absorption such as aluminum monostearate and gelatin.

In some cases, in order to prolong the effect of a drug, it is desirable to slow the absorption of the drug from subcutaneous or intramuscular injection. This may be accomplished by the use of a liquid suspension of crystalline or amorphous material having poor water solubility. The rate of absorption of the drug then depends upon its rate of dissolution, which in turn, may depend upon crystal size and crystalline form. Alternatively, delayed absorption of a parenterally-administered drug form is accomplished by dissolving or suspending the drug in an oil vehicle.

Injectable depot forms are made by forming microencapsule matrices of the subject compounds in biodegradable polymers such as polylactide-polyglycolide. Depending on the ratio of drug to polymer, and the nature of the particular polymer employed, the rate of drug release can be controlled. Examples of other biodegradable polymers include poly(orthoesters) and poly(anhydrides). Depot injectable formulations are also prepared by entrapping the drug in liposomes or microemulsions, which are compatible with body tissue.

In certain embodiments, a DBH inhibitor (e.g., disulfiram or Nepicastat) or pharmaceutical preparation is administered orally. In other embodiments, a DBH inhibitor (e.g., disulfiram or Nepicastat) or pharmaceutical preparation is administered intravenously. Alternative routs of administration include sublingual, intramuscular, and transdermal administrations.

When a DBH inhibitor (e.g., disulfiram or Nepicastat) is administered as a pharmaceutical, to humans and animals, it can be given per se or as a pharmaceutical composition containing, for example, 0.1% to 99.5% (more preferably, 0.5% to 90%) of active ingredient in combination with a pharmaceutically acceptable carrier.

The preparations of the present invention may be given orally, parenterally, topically, or rectally. A DBH inhibitor (e.g., disulfiram or Nepicastat) is of course given in forms suitable for each administration route. For example, a DBH inhibitor (e.g., disulfiram or Nepicastat) may be administered in tablets or capsule form, by injection, inhalation, eye lotion, ointment, suppository, etc. administration by injection, infusion or inhalation; topical by lotion or ointment; and rectal by suppositories. Oral administrations are preferred.

The phrases "parenteral administration" and "administered parenterally" as used herein means modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticulare, subcapsular, subarachnoid, intraspinal and intrasternal injection and infusion.

The phrases "systemic administration," "administered systemically," "peripheral administration," and "administered peripherally" as used herein mean the administration of a compound, drug or other material other than directly into the central nervous system, such that it enters the patient's system and, thus, is subject to metabolism and other like processes, for example, subcutaneous administration.

A DBH inhibitor (e.g., disulfiram or Nepicastat) may be administered to humans and other animals for therapy by any suitable route of administration, including orally, nasally, as by, for example, a spray, rectally, intravaginally, parenterally, intracisternally and topically, as by powders, ointments or drops, including buccally and sublingually.

Regardless of the route of administration selected, a DBH inhibitor (e.g., disulfiram or Nepicastat) which may be used in a suitable hydrated form, and/or the pharmaceutical compositions of the present invention, is formulated into pharmaceutically-acceptable dosage forms by conventional methods known to those of skill in the art.

Actual dosage levels of the active ingredients in the pharmaceutical compositions of a DBH inhibitor (e.g., disulfiram or Nepicastat) may be varied so as to obtain an amount of the active ingredient that is effective to achieve the desired therapeutic response for a particular patient, composition, and mode of administration, without being toxic to the patient.

The selected dosage level will depend upon a variety of factors including the particular salt or isomer composition of a DBH inhibitor (e.g., disulfiram or Nepicastat) used, the route of administration, the time of administration, the rate of excretion or metabolism of the particular composition being employed, the duration of the treatment, other agents, compounds and/or materials used in combination with a DBH inhibitor (e.g., disulfiram or Nepicastat), the age, sex, weight, condition, general health and prior medical history of the patient being treated, and like factors well known in the medical arts.

A physician or veterinarian having ordinary skill in the art can readily determine and prescribe the effective amount of the pharmaceutical composition required. For example, the physician or veterinarian could start doses of a DBH inhibitor (e.g., disulfiram or Nepicastat) employed in the pharmaceutical composition at levels lower than that required to achieve the desired therapeutic effect and then gradually increase the dosage until the desired effect is achieved. Likewise, the physician or veterinarian could start doses of a DBH inhibitor (e.g., disulfiram or Nepicastat) employed in the pharmaceutical composition at levels higher than that required to achieve the desired therapeutic effect and then gradually decrease the dosage until the desired effect is achieved.

In some embodiments, a DBH inhibitor (e.g., disulfiram or Nepicastat) or a pharmaceutical composition thereof is provided to a subject chronically. Chronic treatments include any form of repeated administration for an extended period of time, such as repeated administrations for one or more months, between a month and a year, one or more years, or longer. In many embodiments, a chronic treatment involves administering a DBH inhibitor (e.g., disulfiram or Nepicastat), or a pharmaceutical composition thereof, repeatedly over the life of the subject. Preferred chronic treatments involve regular administrations, for example one or more times a day, one or more times a week, or one or more times a month. In general, a suitable dose such as a daily dose of a DBH inhibitor (e.g., disulfiram or Nepicastat) will be that amount of a DBH inhibitor (e.g., disulfiram or Nepicastat) that is the lowest dose effective to produce a therapeutic effect. Such an effective dose will generally depend upon the factors described above. Generally doses of a DBH inhibitor (e.g., disulfiram or Nepicastat) for a patient, when used for the indicated effects, will range from about 0.0001 to about 100 mg per kg of body weight per day. In some embodiments, the daily dosage will range from about 1 to about 50 mg of compound per kg of body weight. In certain embodiments, the daily dosage will range from about 25 to about 50 mg of compound per kg of body weight. However, lower or higher doses can be used. In some embodiments, the dose administered to a subject may be modified as the physiology of the subject changes due to age, disease progression, weight, or other factors.

If desired, the effective daily dose of the active compound may be administered as two, three, four, five, six, or more sub-doses administered separately at appropriate intervals throughout the day, optionally, in unit dosage forms.

While it is possible for a DBH inhibitor (e.g., disulfiram or Nepicastat) to be administered alone, in some embodiments it is preferable to administer it as a pharmaceutical formulation (composition) as described above.

A DBH inhibitor (e.g., disulfiram or Nepicastat) may be formulated for administration in any convenient way for use in human or veterinary medicine, by analogy with other pharmaceuticals.

According to the invention, a DBH inhibitor (e.g., disulfiram or Nepicastat) can be formulated or administered using methods that help the it cross the blood-brain barrier (BBB) to a greater extent than would occur without a particular formulation of route of administration. The vertebrate brain (and CNS) has a unique capillary system unlike that in any other organ in the body. The unique capillary system has morphologic characteristics which make up the blood-brain barrier (BBB). The blood-brain barrier acts as a system-wide cellular membrane that separates the brain interstitial space from the blood. The unique morphologic characteristics of the brain capillaries that make up the BBB are: (a) epithelial-like high resistance tight junctions which literally cement all endothelia of brain capillaries together, and (b) scanty pinocytosis or transendothelial channels, which are abundant in endothelia of peripheral organs.

The permeability of the blood brain barrier can be increased by administering a blood brain barrier agonist, for example bradykinin (U.S. Pat. No. 5,112,596, incorporated herein in its entirety by reference), or polypeptides called receptor mediated permeabilizers (RMP) (U.S. Pat. No. 5,268,164, incorporated herein in its entirety by reference). Exogenous molecules can be administered to the host's bloodstream parenterally by subcutaneous, intravenous or intramuscular injection or by absorption through a bodily tissue, such as the digestive tract, the respiratory system or the skin. The form in which the molecule is administered (e.g., capsule, tablet, solution, emulsion) depends, at least in part, on the route by which it is administered. The administration of the exogenous molecule to the host's bloodstream and the intravenous injection of the agonist of blood-brain barrier permeability can occur simultaneously or sequentially in time. For example, a therapeutic drug can be administered orally in tablet form while the intravenous administration of an agonist of blood-brain barrier permeability is given later (e.g., between 30 minutes later and several hours later). This allows time for the drug to be absorbed in the gastrointestinal tract and taken up by the bloodstream before the agonist is given to increase the permeability of the blood-brain barrier to the drug. On the other hand, an agonist of blood-brain barrier permeability (e.g., bradykinin) can be administered before or at the same time as an intravenous injection of a drug. Thus, the term "co-administration" is used herein to mean that the agonist of blood-brain barrier and the exogenous molecule will be administered at times that will achieve significant concentrations in the blood for producing the simultaneous effects of increasing the permeability of the blood-brain barrier and allowing the maximum passage of the exogenous molecule from the blood to the cells of the central nervous system).

In some embodiments, a DBH inhibitor (e.g., disulfiram or Nepicastat) can be formulated as a prodrug with a fatty acid carrier (and optionally with another neuroactive drug). The prodrug is stable in the environment of both the stomach and the bloodstream and may be delivered by ingestion. The prodrug passes readily through the blood brain barrier. The prodrug preferably has a brain penetration index of at least two times the brain penetration index of the drug alone. Once in the central nervous system, the prodrug, which preferably is inactive, is hydrolyzed into the fatty acid carrier and the DBH inhibitor (and optionally another drug). The carrier preferably is a normal component of the central nervous system and is inactive and harmless. The DBH inhibitor, once released from the fatty acid carrier, is active. Preferably, the fatty acid carrier is a partially-saturated straight chain molecule having between about 16 and 26 carbon atoms, and more preferably 20 and 24 carbon atoms. Examples of fatty acid carriers are provided in U.S. Pat. Nos. 4,939,174; 4,933,324; 5,994,932; 6,107,499; 6,258,836; and 6,407,137, the disclosures of which are incorporated herein by reference in their entirety.

The administration of a DBH inhibitor (e.g., disulfiram or Nepicastat) or pharmaceutical compositions thereof may be for either prophylactic or therapeutic purposes. When provided prophylactically, a DBH inhibitor (e.g., disulfiram or Nepicastat) is provided in advance of disease symptoms. The prophylactic administration of a DBH inhibitor (e.g., disulfiram or Nepicastat) serves to prevent or reduce the rate of onset of symptoms of ALS. When provided therapeutically, a DBH inhibitor (e.g., disulfiram or Nepicastat) is provided at (or shortly after) the onset of the appearance of symptoms of actual disease. In some embodiments, the therapeutic administration of a DBH inhibitor (e.g., disulfiram or Nepicastat) serves to reduce the severity of the disease.

The function and advantage of these and other embodiments of the present invention will be more fully understood from the examples described below. The following examples are intended to illustrate the benefits of the present invention, but do not exemplify the full scope of the invention.

EXAMPLES

The foregoing has been a description of certain non-limiting embodiments of the invention. Accordingly, it is to be understood that the embodiments of the invention herein described are merely illustrative of the application of the principles of the invention. Reference herein to details of the illustrated embodiments is not intended to limit the scope of the claims.

Example 1. Provided Technologies for Assessing DBH Inhibitors

Favorable results in animal studies support use of existing formulations and routes of administration for disulfiram (Antabuse), Nepicastat, and possibly L-DOPS and/or L-DOPA, in accordance with the present invention for treating certain types of memory loss, for instance memory loss associated with a neurodegeneratige disease, disorder, or condition such as Alzheimer's disease. Each of the above-referenced agents are either FDA approved drugs having well-developed regimes for managing toxicity and safety concerns, or are currently in human clinical trials (Nepicastat is not yet FDA approved, but has been studied in phase II safety and efficacy clinical trials by Biotie Therapeutics Corp., for treatment of PTSD and cocaine addiction). Antabuse, by its effect on acetaldehyde dehydrogenase, leads to great discomfort (and potentially serious consequences) when alcohol is consumed. Thus any treatment regime for AD would have to preclude alcohol consumption. L-DOPA and Antabuse are used in a maintenance mode for approved uses (L-DOPA, 200 mg/day; Antabuse, 250 mg/day). L-DOPS (also known as droxidopa or Northera™) is used in a titrated fashion starting from about 100 mg (TID) to no more than about 600 mg (TID). Nepicastat is used in clinical studies in amounts of up to 120 mg/day. Antabuse is not a specific DBH inhibitor. Notably, the drawbacks of the drug for treatment of AD would be eliminated by use of a drug that specifically inhibited DBH, such as Nepicastat. For both conditions (i.e., PTSD and cocaine addiction), the proposed clinical benefit follows from DBH inhibition. Nepicastat does not inhibit alcohol metabolism and avoids many undesirable side effects of Antabuse and, thus in certain embodiments would be desirable over Antabuse in treatment of AD. In rat studies, Antabuse (100 mg/kg) and Nepicastat (50 mg/kg) were injected intraperitoneally (**Schroeder J P et al, 2010); thus the effect of such injections on brain dopamine levels indicates that the drugs cross the blood-brain barrier.

The present disclosure provides technologies to assess reduction of Aβ pathology or memory deficits (e.g., produced by degeneration of the LC) by Antabuse or Nepicastat. For example, the present disclosure describes use of Heneka's model (Kalinin et al., 2007) in which lesion of the LC (by DSP4) in an AD model (JD APP mouse bred injhouse) produces a 5-fold increase in Aβ plaques within 6 months (starting at 3 months of age) to assess reduction of plaque formation and/or amelioration of memory deficits achieved by DBH inhibitors either alone, or in combination with noradrenaline restoration (by L-DOPS).

Figure 2:
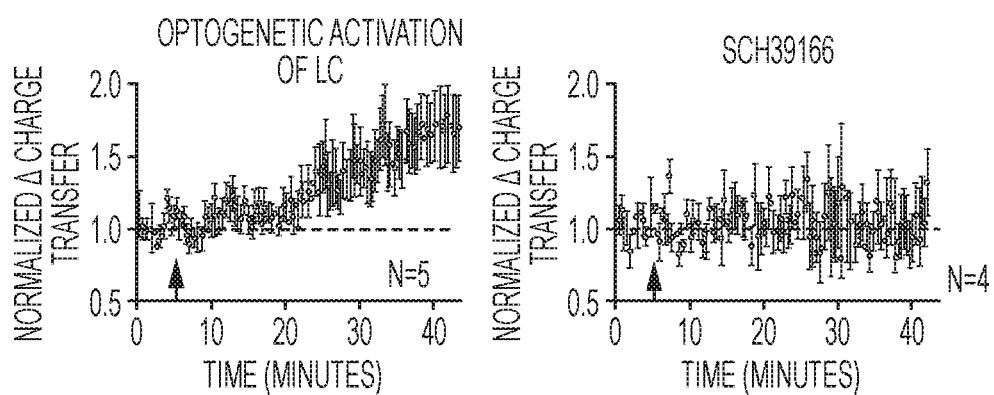
FIG. 2. Results in FIG. 2 document the role of LC axons in producing functionally important dopamine release (Huang and Kandel, 1995). Activation of the LC axons by light produces a form of LTP: long-lasting enhancement of the postsynaptic response (fEPSP).

The present disclosure also provides technologies to assess enhancement of memory by Antabuse or Nepicastat under conditions when LC cell firing is acutely reduced using chemogenetics. The chemogenetic approach allows the acute memory deficits produced by graded decrease in LC function to be measured. This model then provides a rigorous and rapid screening method to determine whether the resulting memory deficits can be reversed by agents that enhance dopamine release (with or without noradrenaline stimulants). Results in FIG. 2 document the role of LC axons in producing functionally important dopamine release. The experiments were done in CA1 using synaptic stimulation of Schaffer collaterals to measure synaptic strength. FIG. 2, left: brief light stimulation of the hippocampus (arrow) produces a long-lasting enhancement of the fEPSP (normalized increase in charge) (n=5). This light-stimulated release of dopamine replicates the effect of direct application of dopamine (Huang and Kandel, 1995). FIG. 2, right: the same light produced no enhancement in the presence of the D1R antagonist SCH39166 (10 uM; n=4). Stimulation protocol: three sets of ~18 Hz stimulation (5 msec light pulses)=a total of 60 pulses/set; 1 minute between sets. The LC was injected in vivo with AAV virus that produced channel-rhodopsin in cells containing tyrosine hydroxylase, an enzyme in the dopamine and noradrenaline synthesis pathway (see FIG. 1). The selective expression in noradrenergic cells in the LC is due to Cre expression driven by a tyrosine hydroxylase promoter. After several weeks, the animal was sacrificed and hippocampal slices cut. By this time, the channel-rhodopsin had been transported from the LC to axon terminals in the hippocampus. To test for dopamine release by these axons, the Schaffer collaterals were stimulated electrically. These collaterals connect CA3 neurons to CA1 neurons. The response of CA1 pyramidal cells was measured by the field EPSP (fEPSP). Each data point is the average of such measurements across n experiments. After establishing a stable baseline, channel-rhodospin was illuminated at the arrow (FIG. 2, left). This results in slowly developing potentiation of the fEPSP. Such slow potentiation is expected from previous work using direct application of dopamine agonist (Huang & Kandel, 1995). When similar experiments were done in the presence of a D1 antagonist (FIG. 2, right), illumination of channel-rhodopsin did not cause potentiation of the fEPSP. Control experiments show that such enhancement is not blocked by noradrenergic antagonists and cannot be mimicked by noradrenergic agonist (Smith & Greene, 2012).

Example 2. Experimental Design and Methods: Determining Whether Aβ Pathology and Memory Deficits can be Reduced by Agents that Enhance Dopamine Release in a System where the LC is Compromised LC deficits using DSP4 produces a 5-fold enhancement of Aβ pathology in the transgenic APP model, as measured at 6 months. We use the J20 transgenic mouse strain which incorporates both the Swedish and the Indiana APP mutations (Mucke et al., 2000), and which is available from the Jackson Laboratory. A colony of these mice are raised at Brandeis. Starting at 3 months, injections of 5 mg/kg of DSP4 are given every two weeks, as in the Heneka experiments. The animals are chronically treated with agents that affect dopamine and noradrenaline in order to see whether the 5-fold enhancement of Aβ pathology can be reduced or prevented. At 9 months, memory is tested in these animals and compared to animals that received a vehicle injection. Animals are then sacrificed and brains removed. In order to confirm that LC damage that has occurred, tyrosine hydroxylase immunohistochemistry is done to determine the extent of the depletion as described in (Kalinin et al., 2007). Aβ pathology of brain sections is tested by immunohistochemistry and biochemical analysis. Immunohistochemistry is done using Aβ antibodies, and plaque morphology are described. For the biochemical assay levels of Aβ, full length APP, and APPα are quantified. Specifically, both Aβ40 and Aβ42 monomers and soluble Aβ oligomers in Tris-buffered saline extracts (post-100,000 g×60 min) of the frozen mouse brain hemispheres are quantified, as routinely done in the Selkoe lab (see (Shankar et al., 2009)). The lab has established several sensitive ELISAs for these species, including a highly Aβ oligomer-selective ELISA. The lab also has ELISAs in place for hAPPs-α, and hAPPs-β; all APP products are normalized to the levels of full-length APP, as determined by WB in the same hippocampal tissue. The fixed hemispheres are used to perform detailed IHC with a series of Aβ isoform-specific antibodies. Further, immunostaining is done for APP+dystrophic neurites, for several tau epitopes for cytoskeletal changes, and several specific markers for microglia and astrocytes. There are 9 animals in each drug group (Table 1).

Behavioral Tests for Memory:

In order to investigate hippocampal memory formation, tests such as the memory test developed in (Wang, Redondo, & Morris, 2010), and/or behavioral tests testing contextual fear, and/or conditioned place avoidance tests are used. This test measures memory acquisition after a single trial and is therefore a good model for episodic memory. Furthermore, the test has been used to demonstrate the dopamine requirement for 1 day memory, the form of memory that we want to understand. The arena is composed of a floor that contains a 7×7 grid with a total of 49 circular sandwells (5 cm in diameter, 20 cm spacing, covered by 3 cm sawdust). Two landmarks are placed in two locations, e.g., row 4 column 2, and row 4 column 6. The starting locations for mice exploration in this environment are four Plexiglas boxes located in the middle of each side of the arena. The circular holes in the floor are filled with either sand or a combination of sand and food pellets (90/10 ratio). During a single encoding trial, mice find a food pellet in a single sandwell into which pellets have been place. During a subsequent retrieval trial, four unrewarded sandwells are uncovered. After the rodent leaves the start box it may go directly to the sandwell that was baited during encoding and digs there exclusively (perfect memory); with less strong memory it may spend time also digging at one of the four other sandwells. If the reward during encoding is high (3 pellets), rodents generally remember well at 24 hours and dig with high preference at the previously rewarded sandwell. In FIG. 4D of Wang et al, it was shown that 24 hr three-pellet memory was blocked by D1/D5 antagonist given during the encoding trial. This protocol is used to quantify whether LC lesion reduces memory and whether this deficit can be ameliorated using agents (Table 1) that affect dopamine and noradrenaline. After encoding trails, the memory trial is at either 30 minutes or at 1 day (interleaved). The purpose of the 30 minute tests is to directly demonstrate that learning occurred and was incorporated in the short-term memory, even under conditions whether lack of dopamine prevented formation of long-term memory, as with the dopamine antagonists. The percent of the digging time spent at each sandwell is video recorded and analyzed blind according to the procedure described in (Wang et al., 2010). These data are used to quantify effects on memory using an ANOVA, as in (Wang et al., 2010).

Example 3. Experimental Design and Methods: Determining Whether Long-Term Memory can be Enhanced by DBH Inhibitors in an Animal Model Having Reduced LC Function It is highly desirable to have an animal model of AD that specifically mimicks the deficit in the LC. In developing such a model, there were several considerations. It was decided not to use an existing AD model because deficits occurred in multiple brain system; thus one could not specifically study drug effects on the LC. A further goal was to have a system suitable for much more rapid testing of agents than the system described above, where experiments require 9 months. Finally, for testing of memory effects it is highly desirable to have temporal control of the LC deficit, thus making it possible to do within-animal studies of memory deficits before, during, and after LC deficits (and thus amelioration of these deficits by agents).

These goals are met by the following system. The work of Patricia Jensen has shown how molecular changes can be introduced genetically that are limited to the LC (and not to other noradrenergic nuclei). The basic strategy is that the LC can be genetically modified in selective way through the expression of control elements of both DBH and the Engrailed 1 gene (Robertson, Plummer, de Marchena, & Jensen, 2013). This is important in insuring that behavioral effects due to changes in other noradrenergic nuclei are not a factor. Jensen has used this system to implement a chemogenetic strategy in which DREADDs are expressed in noradrenerdgic neurons. DREADDs are molecules that change the cell voltage when the receptor is activated by an exogenous ligand. The DREADD is engineered so that it can be activated by a ligand that crosses the blood brain barrier and that has little or no effect on endogenous receptors. Dr. Jensen has made mice that has an excitatory DREADD in the LC; thus when activated by ligand it depolarizes the LC and stimulates noradrenaline release. Dr. Jensen provides a similar mouse that produces hyperpolarization of the LC and thereby inhibits LC release. This DREADD is based on the κ-opiod receptor DREADD, (KORD) that can be selectively activated using salvinorin B (SALB) (Vardy et al., 2015). KORD is a g-protein coupled receptor that leads to the hyperpolarization of the cell, which has been observed in various cell types (Vardy et al., 2015). The hyperpolarization is thought to occur primarily through the activation of inward rectifying potassium channels (Bruchas & Chavkin, 2013). This system has important improvements in selectivity compared to previous generations of DREADDS due to the lack of activation of KORDS by endogenous agonists, and the selectivity of SALB. SALB will be administered subcutaneously (10 mg/kg), a dose has been shown to induce effects shortly after injection and that last for ~1 hr (Vardy et al., 2015).

To quantitatively observe the effects of SALB on membrane potential and excitability, whole-cell electrophysiology is used in a slice preparation to confirm that the construct is working as described in (Vardy et al., 2015). A potassium gluconate-based internal recording solution is used in current-clamp to determine the resting potential for each neuron. A 5 minute baseline is acquired, after which 100 nm SALB are applied at a flow rate of 2 mL/min (Vardy et al., 2015). A stimulating electrode is placed nearby to investigate the effect of SALB on both EPSP and spiking activity.

Once this is determined, in vivo memory experiments are conducted while the LC is being inhibited with SALB and the memory deficit is measured. SALB is injected subcutaneously 10 minutes before tan encoding trail. Based on results with dopamine antagonists, it is expected that inhibition of dopamine function during the brief encoding period will strongly reduce 24 hr memory, but not 30 minutes memory (Wang et al., 2010). Strategies for enhancing dopamine release (Table 2) to partially or fully restore memory function are then tested. In a final step, memory is tested after removal of the SALB to insure than none of the agents produced irreversible effects. Memory function is tested using the same event arena system described above.

Mice are also sent to a collaborator, who uses a different memory assay to evaluate the effects of the KORD system.

TABLE 1

Drug conditions

| | |
|---|---|
| Group 1 | WT + vehicle injection (9 animals) |
| Group 2 | APP mutant + vehicle injection (9 animals) |
| Group 3 | APP mutant + DSP4 (9 animals) |
| Group 4 | APP mutant + DSP4 + Antabuse (H + L dose) (9 animals) |
| Group 5 | APP mutant + DSP4 + Antabuse + L-DOPS (H + L dose) (9 animals) |

In Table 1, (+) indicates that the conditions occur concurrently; H=high dose and L=low dose

TABLE 2

DREADD

| | |
|---|---|
| Group 1 | WT + SALB |
| Group 2 | KORD + SALB + (SALB + Nepicastat) + SALB (6-10 animals) |
| Group 3 | KORD + SALB + (SALB + Antabuse) + SALB (6-10 animals) |
| Group 4 | KORD + SALB + (SALB + nepicastat + L-DOPS) + SALB (6-10 animals) |
| Group 5 | KORD + SALB + (SALB + antabuse + L-DOPS) + SALB (6-10 animals) |

In Table 2, a comma indicates chronologically distinct conditions and + indicates that the agents are used concurrently.

Drug Doses:
Dosing in Example 2, Above:
DSP4 is administered through the protocol outlined in (Kalinin et al., 2007), 5 mg/kg IP injections every 2 weeks for a 6 month period. Nepicastat, Antabuse, and L-DOPS are added to mouse chow for the 6-month period. The approach used herein is based on working from human therapeutic doses and adding the adjusted amount of the drug to the mouse diet. In order to account for the fluctuations in mouse size and feeding patterns two dose regimens are used.

For nepicastat the maximum clinically tested dose is 160 mg (https://www.clinicaltrials.gov/ct2/show/study/NCT00656357), using the standard conversion factor of 12.3 to account for changes in metabolism, and the calculator provided by Research Diet (http://www.researchdiets.com/resource-center-page/) to account for mouse size and chow intake, the two calculated chow concentrations are 150 mg/kg and 200 mg/kg.

For disulfiram, the maintenance dose of 250 mg/day was used (http://www.drugs.com/dosage/disulfiram.html#Usual_adult_Dose_for_alcohol_dependence, and the calculated chow concentrations are 210 mg/kg (low chow concentration) and 280 mg/kg (high chow concentration).

Finally, for L-DOPS (droxydopa), the therapeutic dose in humans is 600 mg/day (http://www.accessdata.fda.gov/drugsatfda_docs/label/2014/203202lbl.pdf), 25 mg/day for benserazide (http://www.medsafe.govt.nz/profs/datasheet/m/Madoparcapdisptab.pdf), and 40 mg/day for atomoxetine (http://www.drugs.com/dosage/atomoxetine.html). As it is desired to use a pre-existing rodent method for L-DOPS application capable of producing a verified elevation of brain noradrenaline levels, the protocol described in (Kalinin et al., 2012) is utilized. In this protocol, L-DOPS is injected together with benserazide (to reduce peripheral conversion) and a noradrenaline reuptake inhibitor atomoxetine. DL-DOPS is dissolved in 0.2 N HCL then neutralized with NaOH, the concentration is 40 mg/mL. Then benserazide is added to the solution to produce a concentration of 12.5 ml/mL; atomoxetine is added to produce a final concentration of 2 mg/mL. Mice receive 200 μL IP injection three times per week, as described in Kalinin et al., 2012. Follow-up experiments are conducted to show the relative importance of the different components of this mixture. Dosages are then adjusted appropriately based on the results of this study.

Dosing in Example 3, Above:
L-DOPS is injected with benserazide (to reduce peripheral conversion), a noradrenalin reuptake inhibitor atomoxetine, as described in Example 2. To test the effects of Nepicastat and Antabuse, IP injections are made at 4 and 2 hr before behavioral testing. This allows sufficient time for drug action (Schroeder et al., 2010). Following Schroeder, Antabuse is sonicated in sterile saline and 10 mg/kg (lowest effective concentration), 25 mg/kg, and 100 mg/kg (highest effective dose that didn't affect operant responses); and injected as a suspension. Nepicastat is sonicated in sterile saline containing 1.5% DMSO and 1.5% Cremaphor EL (Sigma), and doses of 5, 15, and 50 mg/kg are tested. The 50 mg/kg dose was reported to match the 100 mg/kg dose of Antabuse on DBH by Schroeder. SALB is injected subcutaneously at 10 mg/kg.

Example 2 Timeline:

0-6 months: Breed colony of J20 APP mice. Conduct feeding study. Do tests on the dosages used in feeding study to determine catecholamine levels using HPLC 0-8 months: Check DSP4 action in WT 9 months: Start treatment with DSP4 and neuroprotective agents (staggered)

15-21 months: Test memory on DSP4 mice. Sacrifice animals and start sending fixed/frozen hemi-brains to Selkoe lab for analysis of Aβ monomers, oligomers, and APPs-α and -β by specific ELISAs, and quantify plaque burden and associated surrounding neuropathology by IHC.

21-24 months: analyze results

Example 3 Timeline:

0-6 months: Establish a colony of KORD mice 4-8 months: Electrophysiology on LC 5-7 months: Establish behavorial assay with WT 7-18 months: Memory tests on KORD mice 18-24 months: analyze results

REFERENCES

Bethus, I., Tse, D., & Morris, R. G. M. (2010). Dopamine and memory: modulation of the persistence of memory for novel hippocampal NMDA receptor-dependent paired associates. *The Journal of Neuroscience: The Official Journal of the Society for Neuroscience*, 30(5), 1610-1618. http://doi.org/10.1523/JNEUROSCI.2721-09.2010

Bondareff, W., Mountjoy, C. Q., & Roth, M. (1982). Loss of neurons of origin of the adrenergic projection to cerebral cortex (nucleus locus ceruleus) in senile dementia. *Neurology*, 32(2), 164-168. http://doi.org/10.1212/WNL.32.2.164

Bosch, M., Castro, J., Saneyoshi, T., Matsuno, H., Sur, M., & Hayashi, Y. (2014). Structural and Molecular Remodeling of Dendritic Spine Substructures during Long-Term Potentiation. *Neuron*, 82(2), 444-459. http://doi.org/10.1016/j.neuron.2014.03.021

Braak, H., & Del Tredici, K. (2012). Where, when, and in what form does sporadic Alzheimer's disease begin? *Curr Opin Neurol*, 25(6), 708-714. http://doi.org/10.1097/WCO.0b013e32835a3432

Bruchas, M. R., & Chavkin, C. (2013). Kinase Cascades and Ligand-Directed Signaling at the Kappa Opioid Receptor, 210(2), 137-147. http://doi.org/10.1007/s00213-010-1806-y.Kinase Devoto, P., Flore, G., Saba, P., Bini, V., & Gessa, G. L. (2014). The dopamine beta-hydroxylase inhibitor nepicastat increases dopamine release and potentiates psychostimulant-induced dopamine release in the prefrontal cortex. *Addiction Biology*, 19(4), 612-22. http://doi.org/10.1111/adb.12026

Frey, U., Schroeder, H., & Matthies, H. (1990). Dopaminergic antagonists prevent long-term maintenance of posttetanic LTP in the CA1 region of rat hippocampal slices. *Brain Research*, 522, 69-75. http://doi.org/10.1016/0006-8993(90)91578-5

Gannon, M., Che, P., Chen, Y., Jiao, K., Roberson, E. D., & Wang, Q. (2015). Noradrenergic dysfunction in Alzheimer's disease. *Frontiers in Neuroscience*, 9(June), 220. http://doi.org/10.3389/fnins.2015.00220

Gao, H., Sengupta, J., Gao, N., Taylor, D. J., Noller, H. F., Maus, C. E.,

Korostelev, a. (2009). Dopamine Controls Persistence of, 325(August), 1017-1020.

Gaval-Cruz, M., Liles, L. C., Iuvone, P. M., & Weinshenker, D. (2012). Chronic Inhibition of Dopamine ??-Hydroxylase Facilitates Behavioral Responses to Cocaine in Mice. *PLoS ONE*, 7(11), 1-9. http://doi.org/10.1371/journal.pone.0050583

Giese, K. P., Fedorov, N. B., Filipkowski, R. K., & Silva, a J. (1998). Autophosphorylation at Thr286 of the alpha calcium-calmodulin kinase II in LTP and learning. *Science (New York, N.Y.)*, 279(5352), 870-873. http://doi.org/10.1126/science.279.5352.870

Goldstein, M., & Nakajima, K. (1967). THE EFFECT OF DISULFIRAM ON CATECHOLAMINE LEVELS IN THE BRAIN. *J. Pharmacol. Exp. Ther.*, 157(1), 96-102. Retrieved from http://jpet.aspetjournals.org/content/157/1/96.short Hammerschmidt, T., Kummer, M. P., Terwel, D., Martinez, A., Gorji, A., Pape, H.-C., . . . Heneka, M. T. (2013). Selective loss of noradrenaline exacerbates early cognitive dysfunction and synaptic deficits in APP/PS1 mice. *Biological Psychiatry*, 73(5), 454-63. http://doi.org/10.1016/j.biopsych.2012.06.013

Hell, J. W., & Ehlers, M. D. (2008). *Structural and functional organization of the synapse. Structural And Functional Organization Of The Synapse.* http://doi.org/10.1007/978-0-387-77232-5

Hopkins, W. F., & Johnston, D. (1988). Noradrenergic enhancement of long-term potentiation at mossy fiber synapses in the hippocampus. *J Neurophysiol*, 59(2), 667-687. Retrieved from http://jn.physiology.org/content/59/2/667.short Huang, Y. Y., & Kandel, E. R. (1995). D1/D5 receptor agonists induce a protein synthesis-dependent late potentiation in the CA1 region of the hippocampus. *Proceedings of the National Academy of Sciences of the United States of America*, 92(7), 2446-2450. http://doi.org/10.1073/pnas.92.7.2446

Kalinin, S., Gavrilyuk, V., Polak, P. E., Vasser, R., Zhao, J., Heneka, M. T., & Feinstein, D. L. (2007). Noradrenaline deficiency in brain increases β-amyloid plaque burden in an animal model of Alzheimer's disease. *Neurobiology of Aging*, 28, 1206-1214. http://doi.org/10.1016/j.neurobiolaging.2006.06.003

Kalinin, S., Polak, P. E., Lin, S. X., Sakharkar, A. J., Pandey, S. C., & Feinstein, D. L. (2012). The noradrenaline precursor L-DOPS reduces pathology in a mouse model of Alzheimer's disease. *Neurobiology of Aging*, 33(8), 1651-1663. http://doi.org/10.1016/j.neurobiolaging.2011.04.012

Li, S., Cullen, W. K., Anwyl, R., & Rowan, M. J. (2003). Dopamine-dependent facilitation of LTP induction in hippocampal CA1 by exposure to spatial novelty. *Nature Neuroscience*, 6(5). http://doi.org/10.1038/nn1049

Li, S., Jin, M., Zhang, D., Yang, T., Koeglsperger, T., Fu, H., & Selkoe, D. J. (2013). Environmental novelty activates β2-adrenergic signaling to prevent the impairment of hippocampal LTP by Aβ oligomers. *Neuron*, 77(5), 929-941. http://doi.org/10.1016/j.neuron.2012.12.040

Lisman, J., Grace, A. a., & Duzel, E. (2011). A neoHebbian framework for episodic memory; role of dopamine-dependent late LTP. *Trends in Neurosciences*, 34(10), 536-547. http://doi.org/10.1016/j.tins.2011.07.006

Lockrow, J. P., Fortress, A. M., & Granholm, A.-C. E. (2012). Age-related neurodegeneration and memory loss in down syndrome. *Current Gerontology and Geriatrics Research,* 2012, 463909. http://doi.org/10.1155/2012/463909

Marien, M. R., Colpaert, F. C., & Rosenquist, A. C. (2004). Noradrenergic mechanisms in neurodegenerative diseases: A theory. *Brain Research Reviews,* 45(1), 38-78. http://doi.org/10.1016/j.brainresrev.2004.02.002

Mingote, S., Chuhma, N., Kusnoor, S., Field, B., Deutch, A., & Rayport, S. (2012). VTA Dopamine Neuron Excitatory Functional Connectome. In *Champalimaud Neuroscience Symposium Lisbon, Portugal.*

Moudy, a M., Kunkel, D. D., & Schwartzkroin, P. a. (1993). Development of dopamine-beta-hydroxylase-positive fiber innervation of the rat hippocampus. *Synapse* (New York, N.Y.), 15(4), 307-18. http://doi.org/10.1002/syn.890150407

Mucke, L., Masliah, E., Yu, G. Q., Mallory, M., Rockenstein, E. M., Tatsuno, G., . . . McConlogue, L. (2000). High-level neuronal expression of abeta 1-42 in wild-type human amyloid protein precursor transgenic mice: synaptotoxicity without plaque formation. *The Journal of Neuroscience: The Official Journal of the Society for Neuroscience,* 20(11), 4050-4058. http://doi.org/20/11/4050 [pii]

Musacchio, J. M., Goldstein, M., Anagnoste, B., Poch, G., & Kopin, I. J. (1966). Inhibition of dopamine-beta-hydroxylase by disulfiram in vivo. *The Journal of Pharmacology and Experimental Therapeutics,* 152(1), 56-61.

Nicoll, R. a. (2003). Expression mechanisms underlying long-term potentiation: a postsynaptic view. *Philosophical Transactions of the Royal Society of London. Series B, Biological Sciences,* 358(1432), 721-726. http://doi.org/10.1098/rstb.2002.1228

Ortiz, O., Delgado-Garcia, J. M., Espadas, I., Bahi, A., Trullas, R., Dreyer, J.-L., . . . Moratalla, R. (2010). Associative learning and CA3-CA1 synaptic plasticity are impaired in D1R null, Drd1a−/− mice and in hippocampal siRNA silenced Drd1a mice. *The Journal of Neuroscience: The Official Journal of the Society for Neuroscience,* 30(37), 12288-12300. http://doi.org/10.1523/JNEUROSCI.2655-10.2010

Otmakhova, N. a, & Lisman, J. E. (1998). D1/D5 dopamine receptors inhibit depotentiation at CA1 synapses via cAMP-dependent mechanism. *The Journal of Neuroscience: The Official Journal of the Society for Neuroscience,* 18(4), 1270-1279.

Robertson, S. D., Plummer, N. W., de Marchena, J., & Jensen, P. (2013). Developmental origins of central norepinephrine neuron diversity. *Nature Neuroscience,* 16(8), 1016-1023. http://doi.org/10.1038/nn.3458

Ross, S. B., & Stenfors, C. (2015). DSP4, a selective neurotoxin for the locus coeruleus noradrenergic system. A review of its mode of action. *Neurotoxicity Research,* 27(1), 15-30. http://doi.org/10.1007/s12640-014-9482-z Schroeder, J. P., Cooper, D. a, Schank, J. R., Lyle, M. a, Gaval-Cruz, M., Ogbonmwan, Y. E., . . . Weinshenker, D. (2010). Disulfiram attenuates drug-primed reinstatement of cocaine seeking via inhibition of dopamine β-hydroxylase. *Neuropsychopharmacology: Official Publication of the American College of Neuropsychopharmacology,* 35(12), 2440-2449. http://doi.org/10.1038/npp.2010.127

Smith, C. C., & Greene, R. W. (2012). CNS Dopamine Transmission Mediated by Noradrenergic Innervation. *Journal of Neuroscience,* 32(18), 6072-6080. http://doi.org/10.1523/JNEUROSCI.6486-11.2012

Sonneborn, A., Hamilton, C., & Greene, R. W. (2015). A physiological role for locus coeruleus dopamine. In *Society for Neuroscience.*

Stanley, W. C., Li, B., Bonhaus, D. W., Johnson, L. G., Lee, K., Porter, S., . . . Hegde, S. S. (1997). Catecholamine modulatory effects of nepicastat (RS-25560-197), a novel, potent and selective inhibitor of dopamine-β-hydroxylase. *British Journal of Pharmacology,* 121(8), 1803-1809. http://doi.org/10.1038/sj.bjp.0701315

Szot, P., White, S., Greenup, L., Leverenz, J., Peskind, E., & Raskind, M. (2006). Compensatory Changes in the Noradrenergic Nervous System in the Locus Ceruleus and Hippocampus of Postmortem Subjects with Alzheimer's Disease and Dementia with Lewy Bodies. *Journal of Neuroscience,* 26(2), 467-478. http://doi.org/10.1523/JNEUROSCI.4265-05.2006

Takeuchi, T., Duszkiewicz, A. J., Yamasaki, M., Tse, D., Spooner, P., Watanabe, M., . . . Morris, R. G. M. (2015). Catecholaminergic enchancement of initial memory consolidation in mice. In *Society for Neuroscience.*

Thomas, S. a, & Palmiter, R. D. (1997). Disruption of the dopamine beta-hydroxylase gene in mice suggests roles for norepinephrine in motor function, learning, and memory. *Behavioral Neuroscience,* 111(3), 579-589.

Vardy, E., Robinson, J. E., Li, C., Olsen, R. H. J., DiBerto, J. F., Giguere, P. M., . . . Roth, B. L. (2015). A New DREADD Facilitates the Multiplexed Chemogenetic Interrogation of Behavior. *Neuron,* 86(4), 936-946. http://doi.org/10.1016/j.neuron.2015.03.065

Wang, S.-H., Redondo, R. L., & Morris, R. G. M. (2010). Relevance of synaptic tagging and capture to the persistence of long-term potentiation and everyday spatial memory. *Proceedings of the National Academy of Sciences of the United States of America,* 107(45), 19537-19542. http://doi.org/10.1073/pnas.1008638107

Zarow, C., Lyness, S. A., Mortimer, J. A., & Chui, H. C. (2003). Neuronal loss is greater in the locus coeruleus than nucleus basalis and substantia nigra in Alzheimer and Parkinson diseases. *Archives of Neurology,* 60(3), 337-341. http://doi.org/10.1001/archneur.60.3.337

EQUIVALENTS

Having described some illustrative embodiments of the invention, it should be apparent to those skilled in the art that the foregoing is merely illustrative and not limiting, having been presented by way of example only. Numerous modifications and other illustrative embodiments are within the scope of one of ordinary skill in the art and are contemplated as falling within the scope of the invention. In particular, although many of the examples presented herein involve specific combinations of method acts or system elements, it should be understood that those acts and those elements may be combined in other ways to accomplish the same objectives. Acts, elements, and features discussed only in connection with one embodiment are not intended to be excluded from a similar role in other embodiments. Further, for the one or more means-plus-function limitations recited in the following claims, the means are not intended to be limited to the means disclosed herein for performing the recited function, but are intended to cover in scope any means, known now or later developed, for performing the recited function.

Use of ordinal terms such as "first", "second", "third", etc., in the claims to modify a claim element does not by itself connote any priority, precedence, or order of one claim element over another or the temporal order in which acts of a method are performed, but are used merely as labels to distinguish one claim element having a certain name from another element having a same name (but for use of the ordinal term) to distinguish the claim elements. Similarly, use of a), b), etc., or i), ii), etc. does not by itself connote any priority, precedence, or order of steps in the claims. Similarly, the use of these terms in the specification does not by itself connote any required priority, precedence, or order.

The foregoing written specification is considered to be sufficient to enable one skilled in the art to practice the invention. The present invention is not to be limited in scope by examples provided, since the examples are intended as a single illustration of one aspect of the invention and other functionally equivalent embodiments are within the scope of the invention. Various modifications of the invention in addition to those shown and described herein will become apparent to those skilled in the art from the foregoing description and fall within the scope of the appended claims. The advantages and objects of the invention are not necessarily encompassed by each embodiment of the invention.

I claim:

1. A method comprising the step of:
   administering to a subject suffering from or susceptible to memory loss associated with a neurodegenerative disease, disorder, or condition
   an effective amount of a DBH inhibitor, wherein the DBH inhibitor is a selective DBH inhibitor;
   wherein the subject is receiving or has previously received one or more agents that ameliorate noradrenaline reduction associated with use of a DBH inhibitor; and
   wherein the subject receives chronic administration of both the selective DBH inhibitor and the one or more agents that ameliorate noradrenaline reduction associated with use of a DBH inhibitor;
   such that the severity or incidence of memory loss is reduced, or its onset is delayed.

2. The method of claim 1, wherein the neurodegenerative disease, disorder, or condition is associated with reduced dopamine levels in the locus coeruleus (LC).

3. The method of claim 1, wherein the neurodegenerative disease, disorder, or condition is Alzheimer's Disease.

4. The method of claim 1, wherein the Alzheimer's disease is early stage Alzheimer's Disease.

5. A method comprising the step of:
   administering to a subject suffering from or susceptible to memory loss associated with degeneration of the locus coeruleus (LC) an effective amount of a DBH inhibitor, wherein the DBH inhibitor is a selective DBH inhibitor;
   wherein the subject is receiving or has previously received one or more agents that ameliorate noradrenaline reduction associated with use of a DBH inhibitor; and
   wherein the subject receives chronic administration of both the selective DBH inhibitor and the one or more agents that ameliorate noradrenaline reduction associated with use of a DBH inhibitor;
   such that the severity or incidence of memory loss is reduced, or its onset is delayed.

6. The method of claim 1, wherein the DBH inhibitor is Nepicastat.

7. The method of claim 1, wherein the one or more agents that ameliorate noradrenaline reduction associated with use of a DBH inhibitor is L-DOPS.

8. The method of claim 1, further comprising administration of one or more agents or therapies known to increase levels of dopamine in a subject.

9. The method of claim 8, wherein the administration of the one or more agents or therapies known to increase levels of dopamine in a subject comprises administration of L-DOPA to the subject.

10. The method of claim 1, further comprising administration of one or more agents or therapies known to inhibit reuptake of dopamine in a subject.

11. The method of claim 10, wherein the one or more agents or therapies known to inhibit reuptake of dopamine in a subject is selected from altropane (O-587), amfonelic acid (WIN 25978), aminaptine, BTCP (GK-13), DBL-583, difluoropine (O-620), GBR-12783, GBR-12935, GBR-13069, GBR-13098, GYKI-52895, lometopane (beta-CIT, RTI-55), methylphenidate, RTI-229, and vanoxerine (GBR-12909).

12. The method of claim 1, wherein the method prevents or reduces amyloid beta plaque formation as compared to an untreated subject.

13. The method of claim 1, wherein the DBH inhibitor is administered in doses ranging from about 1 mg/kg/day to about 40 mg/kg/day.

14. The method of claim 1, wherein the DBH inhibitor is administered in doses ranging from about 0.0001 mg/kg/day to about 100 mg/kg/day.

15. The method of claim 1, wherein the DBH inhibitor is administered orally.

16. The method of claim 15, wherein the DBH inhibitor is administered orally once or twice daily.

17. The method of claim 1, wherein the DBH inhibitor is administered to the subject repeatedly for one or more months.

18. The method of claim 1, wherein the DBH inhibitor is administered to the subject repeatedly for between one month and one or more years.

19. The method of claim 1, wherein the DBH inhibitor is administered to the subject repeatedly over the life of the subject.

20. The method of claim 1, wherein the DBH inhibitor is Nepicastat and the one or more agents that ameliorate noradrenaline reduction associated with use of a DBH inhibitor is L-DOPS.

* * * * *